US012351806B2

(12) United States Patent
Papadakis et al.

(10) Patent No.: US 12,351,806 B2
(45) **Date of Patent: *Jul. 8, 2025**

(54) HMO PRODUCTION

(71) Applicant: GLYCOM A/S, Hørsholm (DK)

(72) Inventors: Manos Papadakis, Brønshøj (DK); Katrine Bych Kampmann, Valby (DK)

(73) Assignee: GLYCOM A/S, Horsholm (DK)

( * ) Notice: Subject to any disclaimer, the term of this patent is extended or adjusted under 35 U.S.C. 154(b) by 370 days.

This patent is subject to a terminal disclaimer.

(21) Appl. No.: 17/759,261

(22) PCT Filed: Jan. 22, 2021

(86) PCT No.: PCT/EP2021/051468

§ 371 (c)(1),
(2) Date: Jul. 21, 2022

(87) PCT Pub. No.: WO2021/148611

PCT Pub. Date: Jul. 29, 2021

(65) Prior Publication Data

US 2023/0046359 A1 Feb. 16, 2023

(30) Foreign Application Priority Data

Jan. 23, 2020 (DK) .......................... PA 2020 00087

(51) Int. Cl.

| | |
|---|---|
| ***C12N 15/70*** | (2006.01) |
| ***C07H 3/06*** | (2006.01) |
| ***C12N 5/10*** | (2006.01) |
| ***C12N 15/74*** | (2006.01) |
| ***C12P 19/00*** | (2006.01) |
| ***C12P 19/02*** | (2006.01) |
| ***C12P 19/18*** | (2006.01) |

(52) U.S. Cl.
CPC .............. *C12N 15/70* (2013.01); *C12P 19/02* (2013.01)

(58) Field of Classification Search
CPC .......... C12N 15/70; C12N 5/10; C12N 15/74; C12N 19/02; C07H 3/06
See application file for complete search history.

(56) References Cited

U.S. PATENT DOCUMENTS

| | | | |
|---|---|---|---|
| 10,519,475 B1 | 12/2019 | Walter et al. | |
| 11,898,185 B2 * | 2/2024 | Jennewein | C12Y 101/01271 |
| 2005/0094610 A1 | 5/2005 | De Clerq et al. | |
| 2018/0321354 A1 | 11/2018 | Patel et al. | |
| 2019/0119314 A1 | 4/2019 | Chassagne et al. | |
| 2019/0323052 A1 | 10/2019 | Hollands et al. | |
| 2019/0323053 A1 | 10/2019 | Lafend et al. | |

FOREIGN PATENT DOCUMENTS

| | | |
|---|---|---|
| EP | 3461890 | 4/2019 |
| EP | 3569713 | 11/2019 |
| WO | WO 2010142305 | 12/2010 |
| WO | WO 2012112777 | 8/2012 |
| WO | WO 2015150328 | 10/2015 |
| WO | WO 2015188834 | 12/2015 |
| WO | WO 2016040531 | 3/2016 |
| WO | WO 2016095924 | 6/2016 |
| WO | WO 2017042382 | 3/2017 |
| WO | WO 2017152918 | 9/2017 |
| WO | WO 2017182965 | 10/2017 |
| WO | WO 2018077892 | 5/2018 |
| WO | WO 2019123324 | 6/2019 |

OTHER PUBLICATIONS

Genbank, "MFS transporter [Pantoea vagans]", Accession No. WP_048785139.1, Jun. 9, 2016.
Altschul et al. Nucl. Acids Res. 25, 3389 (1997).
Chen, Adv. Carbohydr. Chem. Biochem. 72, 113 (2015).
Chichlowski M. et al, (2012) J. Pediatr. Gastroenterol. Nutr. 5:251-258.
Elison E. et al, (2016) Brit J. Nutr, 116: 1356-1368.
Gebus C et al (2012) Carbohydrate Research 363 83-90.
Genbank, "glycosyltransferase [Helicobacter pylori 26695]," Accession No. NP_207619.1, Aug. 2, 2016.
Genbank, "predicted N-acetylmannosamine kinase [*Escherichia coli* str. K-12 substr. W3110]," Accession No. BAE77265.1, Jun. 12, 2014.
Genbank, cytidylyltransferase domain-containing protein [Vibrio brasiliensis] Accession No. 493937153, Mar. 2, 2025.
Genbank, "lacto-N-neotetraose biosynthesis glycosyl transferase LgtB [Neisseria meningitidis MC58]," Accession No. AAF42257.1, Jan. 31, 2014.
Genbank, "lacto-N-neotetraose biosynthesis glycosyl transferase LgtA [Neisseria meningitidis MC58]," Accession No. AAF42258.1, Jan. 31, 2014.
Genbank, "putative sialic acid synthase [Campylobacter jejuni]," Accession No. AAK91726.1, Jul. 23, 2016.
Genbank, "putative N-acetylglucosamine-6-phosphate 2-epimerase [Campylobacter jejuni]," Accession No. AAK91727.1, Jul. 23, 2016.
Genbank, "CMP-Neu5Ac synthetase [Campylobacter jejuni]," Accession No. AAK91728.1, Jul. 23, 2016.
Genbank, "*Streptococcus agalactiae* cpslbD, cpslbF, cpslbG, cpslbH, cpslbI, cpslbJ, cpslbK, cpslbL, neuB, neuC genes, complete cds," Accession No. AB050723.1. Jul. 14, 2016.
Genbank, "glycosyl transferase LgtA [Neisseria gonorrhoeae NCCP11945]," Accession No. ACF31229.1, Jan. 31, 214.

(Continued)

*Primary Examiner* — Maryam Monshipouri
(74) *Attorney, Agent, or Firm* — Neal, Gerber & Eisenberg LLP

(57) ABSTRACT

The present inventive concept relates to a genetically modified cell enabled for the production of an oligosaccharide, preferably, an HMO, comprising a recombinant nucleic acid encoding a protein of the MFS superfamily; and methods using said cell for the production the oligosaccharide, preferably an HMO.

18 Claims, 4 Drawing Sheets

Specification includes a Sequence Listing.

(56) References Cited

OTHER PUBLICATIONS

Genbank, "beta-(1,3)-galactyltransferase, partial [Helicobacter pylori]," Accession No. AEZ55696.1, Mar. 23, 2012.
Genbank, "*E. coli* gene lacZ coding for beta-galactosidase (EC 3.2.1.23)," Accession No. V00296, Jul. 26, 2016.
Genbank, "Multispecies: glycosyltransferase [Enterobacteriaceae]," Accession No. WP_000582563.1, Sep. 2, 2024.
Genbank, "Multispecies: MFS transporter [Pantoea]," Accession No. WP_048785139.1, Aug. 22, 2024.
Genbank, "UDP-N-acetylglucosamine 2-epimerase [*Escherichia coli* S88]," Accession No. YP_002392936.1, Dec. 16, 2014.
Herring, C.D., Glasner, J.D. and Blattner, F.R. (2003). Gene (311). 153-163.
Kunz C. et al., (2014) Food Oligosaccharides: Production, Analysis and Bioactivity, 1st Edition, p. 5-20, Eds. Moreno J. and Luz Sanz M., John Wiley & Sons, Ltd.
Lv et al., Bioprocess Biosyst Eng (2016) 39:1737-1747.
Murphy, J Bacteriol,,(1998);180(8):2063-7.
Muyrers et al., EMBO Rep. (2000) 1(3): 239-243.
Reddy V.S. et al., (2012), FEBS J. 279(11): 2022-2035.
Urashima et al.: Milk Oligosaccharides. Nova Science Publisher (2011).
Vetcher et al., Appl Environ Microbiol. (2005);71(4):1829-35).
Waddell C.S. and Craig N.L., Genes Dev. Feb. 1988;2(2):137-49.
Walterson Alyssa M et al, "Pantoea: insights into a highly versatile and diverse genus within the Enterobacteriaceae", Jan. 1, 2015 (Jan. 1, 2015), vol. 027, No. 39, p. 968-984.
Wenzel et al., Chem Biol. (2005), 12(3):349-56.
Yañez-Ñeco et al., "Galactooligosaccharide Production from Pantoea anthophila Strains Isolated from "Tejuino", a Mexican Traditional Fermented Beverage", *Catalysts*, vol. 7, No. 8, Aug. 22, 2017 (Aug. 22, 2017), p. 242.
Zhang et al., Nature Genetics (1998) 20: 123-128.

* cited by examiner

SEQ ID NO: 1

MKSLLTRKRRINPVFLAFMAASFMIGVAGALQAPTLSLFLTREVQARPLWVGLFFTV
NAIAGIVVSMLVAKRSDSRGDRRTLILFCCAMAFCNALLFAFTRHYLTLITLGVLLSAL
ASVSMPQIFALAREYADQSAREAVMFSSVMRAQLSLAWVIGPPLSFALALNFGFVT
LFLVAAALFLVCILLIKFTLPSVPRAEPLMRSGGMPLSGWRDRDVRLLFIASVTMWT
CNTMYIIDMPLYISVTLGLPEKLAGLLMGTAAGLEIPVMLLAGHYAKRVGKRNLMLIA
VAAGVLFYAGLAMFASQTALMALQLFNAVFIGIIAGIGMLWFQDLMPGRPGAATTMF
TNSISTGMILAGVIQGTLSERFGHIAVYWLALGLAVAAFAMSARVKNV

FIGURE 4

SEQUENCE LISTING

<160> NUMBER OF SEQ ID NOS: 29

<210> SEQ ID NO 1
<211> LENGTH: 392
<212> TYPE: PRT
<213> ORGANISM: Pantoea vagans
<220> FEATURE:
<223> OTHER INFORMATION: vag_WP_048785139.1\optimized translation:

<400> SEQUENCE: 1

Met Lys Ser Leu Leu Thr Arg Lys Arg Arg Ile Asn Pro Val Phe Leu
1 5 10 15

Ala Phe Met Ala Ala Ser Phe Met Ile Gly Val Ala Gly Ala Leu Gln
20 25 30

Ala Pro Thr Leu Ser Leu Phe Leu Thr Arg Glu Val Gln Ala Arg Pro
35 40 45

Leu Trp Val Gly Leu Phe Phe Thr Val Asn Ala Ile Ala Gly Ile Val
50 55 60

Val Ser Met Leu Val Ala Lys Arg Ser Asp Ser Arg Gly Asp Arg Arg
65 70 75 80

Thr Leu Ile Leu Phe Cys Cys Ala Met Ala Phe Cys Asn Ala Leu Leu
85 90 95

Phe Ala Phe Thr Arg His Tyr Leu Thr Leu Ile Thr Leu Gly Val Leu
100 105 110

Leu Ser Ala Leu Ala Ser Val Ser Met Pro Gln Ile Phe Ala Leu Ala
115 120 125

Arg Glu Tyr Ala Asp Gln Ser Ala Arg Glu Ala Val Met Phe Ser Ser
130 135 140

Val Met Arg Ala Gln Leu Ser Leu Ala Trp Val Ile Gly Pro Pro Leu
145 150 155 160

Ser Phe Ala Leu Ala Leu Asn Phe Gly Phe Val Thr Leu Phe Leu Val
165 170 175

Ala Ala Ala Leu Phe Leu Val Cys Ile Leu Leu Ile Lys Phe Thr Leu
180 185 190

Pro Ser Val Pro Arg Ala Glu Pro Leu Met Arg Ser Gly Gly Met Pro
195 200 205

Leu Ser Gly Trp Arg Asp Arg Asp Val Arg Leu Leu Phe Ile Ala Ser
210 215 220

Val Thr Met Trp Thr Cys Asn Thr Met Tyr Ile Ile Asp Met Pro Leu
225 230 235 240

-continued

```
Tyr Ile Ser Val Thr Leu Gly Leu Pro Glu Lys Leu Ala Gly Leu Leu
                245                 250                 255

Met Gly Thr Ala Ala Gly Leu Glu Ile Pro Val Met Leu Leu Ala Gly
            260                 265                 270

His Tyr Ala Lys Arg Val Gly Lys Arg Asn Leu Met Leu Ile Ala Val
        275                 280                 285

Ala Ala Gly Val Leu Phe Tyr Ala Gly Leu Ala Met Phe Ala Ser Gln
    290                 295                 300

Thr Ala Leu Met Ala Leu Gln Leu Phe Asn Ala Val Phe Ile Gly Ile
305                 310                 315                 320

Ile Ala Gly Ile Gly Met Leu Trp Phe Gln Asp Leu Met Pro Gly Arg
                325                 330                 335

Pro Gly Ala Ala Thr Thr Met Phe Thr Asn Ser Ile Ser Thr Gly Met
            340                 345                 350

Ile Leu Ala Gly Val Ile Gln Gly Thr Leu Ser Glu Arg Phe Gly His
        355                 360                 365

Ile Ala Val Tyr Trp Leu Ala Leu Gly Leu Ala Val Ala Ala Phe Ala
    370                 375                 380

Met Ser Ala Arg Val Lys Asn Val
385                 390
```

<210> SEQ ID NO 2
<211> LENGTH: 1182
<212> TYPE: DNA
<213> ORGANISM: Pantoea vagans
<220> FEATURE:
<223> OTHER INFORMATION: vag nucleotide sequence

<400> SEQUENCE: 2

```
atgaagagcg cgctgacctt cagccgtcgt attaacccgg tttttctggc gttctttgtg     60

gttgcgttcc tgagcggtat tgcgggtgcg ctgcaggcgc cgaccctgag cctgttcctg    120

agcaccgagg tgaaagttcg tccgctgtgg gtgggcctgt tctacaccgt taacgcgatt    180

gcgggtatca ccgtgagctt tgttctggcg aagcgtagcg acctgcgtgg cgatcgtcgt    240

aaactgatcc tggtgtgcta cctgatggcg gttggtaact gcctgctgtt cgcgtttaac    300

cgtgactatc tgaccctgat taccgcgggc gtgctgctgg cggcggttgc gaacaccgcg    360

atgccgcaga ttttcgcgct ggcgcgtgag tacgcggata acagcgcgcg tgaagtggtt    420

atgtttagca gcattatgcg tgcgcaactg agcctggcgt gggttatcgg tccgccgctg    480

agcttcatgc tggcgctgaa ctatggcttc accctgatgt tttgcattgc ggcgggtatc    540

ttcgtgctga gcgcgctggt tgtgtggttt attctgccga gcgtgcagcg tgcggaaccg    600

gttatggatg cgccgaccgt ggcgcaaggc agcctgttcg cggacaagga tgttctgctg    660

ctgtttattg cgagcatgct gatgtggacc tgcaacacca tgtacatcat tgatatgccg    720

ctgtatatca ccgcgagcct gggtctgccg gagcgtctgg cgggtctgct gatgggcacc    780

gcggcgggtc tggaaatccc gattatgctg ctggcgggct acagcgtgcg tcgttttggc    840

aagcgtaaaa tcatgctgtt cgcggtgctg gcgggcgttc tgttttatac cggtctggtt    900

ctgttcaagt ttaaaagcgc gctgatgctg ctgcagattt tcaacgcgat ctttattggt    960

atcgtggcgg gtatcggcat gctgtacttc caagacctga tgccgggtcg tgcgggtgcg   1020

gcgaccaccc tgtttaccaa cagcattagc accggcgtta tcctggcggg cgtgctgcaa   1080

ggtgttctga ccgaaacctg ggtcacaac agcgtgtatg ttatggcgat gattctggcg    1140
```

-continued

```
atcctgagcc tgatcatttg cgcgcgtgtg cgtgaagcgt aa                      1182


<210> SEQ ID NO 3
<211> LENGTH: 300
<212> TYPE: DNA
<213> ORGANISM: Artificial Sequence
<220> FEATURE:
<223> OTHER INFORMATION: PglpF regulatory sequence

<400> SEQUENCE: 3

gcggcacgcc ttgcagatta cggtttgcca cacttttcat ccttctcctg gtgacataat     60

ccacatcaat cgaaaatgtt aataaatttg ttgcgcgaat gatctaacaa acatgcatca    120

tgtacaatca gatggaataa atggcgcgat aacgctcatt ttatgacgag gcacacacat    180

tttaagttcg atatttctcg tttttgctcg ttaacgataa gtttacagca tgcctacaag    240

catcgtggag gtccgtgact ttcacgcata caacaaacat taaccaagga ggaaacagct    300


<210> SEQ ID NO 4
<211> LENGTH: 195
<212> TYPE: DNA
<213> ORGANISM: Artificial Sequence
<220> FEATURE:
<223> OTHER INFORMATION: Plac expression element

<400> SEQUENCE: 4

atgcgcaaat tgtgagttag ctcactcatt aggcacccca ggctttacac tttatgcttc     60

cggctcgtat gttgtgtgga attgtgagcg gataacaatt tcacacagga aacagctatg    120

accatgatta cgccaagcgc gcaattaacc ctcactaaag ggaacaaaag ctgggtacct    180

aaggaggaaa cagct                                                      195


<210> SEQ ID NO 5
<211> LENGTH: 34
<212> TYPE: DNA
<213> ORGANISM: Artificial Sequence
<220> FEATURE:
<223> OTHER INFORMATION: Primer O40 backbone.for
<220> FEATURE:
<221> NAME/KEY: misc_RNA
<222> LOCATION: 9

<400> SEQUENCE: 5

attaacccuc caggcatcaa ataaaacgaa aggc                                 34


<210> SEQ ID NO 6
<211> LENGTH: 32
<212> TYPE: DNA
<213> ORGANISM: Artificial Sequence
<220> FEATURE:
<223> OTHER INFORMATION: Primer O68, Plac.for

<400> SEQUENCE: 6

atgcgcaaau tgtgagttag ctcactcatt ag                                   32


<210> SEQ ID NO 7
<211> LENGTH: 32
<212> TYPE: DNA
<213> ORGANISM: Artificial Sequence
<220> FEATURE:
<223> OTHER INFORMATION: Primer O79 Backbone.rev
<220> FEATURE:
<221> NAME/KEY: misc_RNA
<222> LOCATION: 10

<400> SEQUENCE: 7
```

atttgcgcau caccaatcaa attcacgcgg cc 32

<210> SEQ ID NO 8
<211> LENGTH: 36
<212> TYPE: DNA
<213> ORGANISM: Artificial Sequence
<220> FEATURE:
<223> OTHER INFORMATION: Primer O113, Plac.rev

<400> SEQUENCE: 8
agctgttucc tccttaggta cccagctttt gttccc 36

<210> SEQ ID NO 9
<211> LENGTH: 32
<212> TYPE: DNA
<213> ORGANISM: Artificial Sequence
<220> FEATURE:
<223> OTHER INFORMATION: Primer O261, PglpF.for
<220> FEATURE:
<221> NAME/KEY: misc_RNA
<222> LOCATION: 10

<400> SEQUENCE: 9
atgcgcaaau gcggcacgcc ttgcagatta cg 32

<210> SEQ ID NO 10
<211> LENGTH: 36
<212> TYPE: DNA
<213> ORGANISM: Artificial Sequence
<220> FEATURE:
<223> OTHER INFORMATION: Primer O262, PglpF.rev
<220> FEATURE:
<221> NAME/KEY: misc_RNA
<222> LOCATION: 8

<400> SEQUENCE: 10
agctgttucc tccttggtta atgtttgttg tatgcg 36

<210> SEQ ID NO 11
<211> LENGTH: 33
<212> TYPE: DNA
<213> ORGANISM: Artificial Sequence
<220> FEATURE:
<223> OTHER INFORMATION: Primer KABY745, vag.for

<400> SEQUENCE: 11
aaacagcuat gaagagcctg ctgacccgta aac 33

<210> SEQ ID NO 12
<211> LENGTH: 31
<212> TYPE: DNA
<213> ORGANISM: Artificial Sequence
<220> FEATURE:
<223> OTHER INFORMATION: Primer KABY746, vag.rev
<220> FEATURE:
<221> NAME/KEY: misc_RNA
<222> LOCATION: 9

<400> SEQUENCE: 12
agggttaaut taaacgtttt tcacacgcgc g 31

<210> SEQ ID NO 13
<211> LENGTH: 32
<212> TYPE: DNA
<213> ORGANISM: Artificial Sequence
<220> FEATURE:
<223> OTHER INFORMATION: Primer KABY721, yberC0001_9420.for -continued
<220> FEATURE:
<221> NAME/KEY: misc_RNA
<222> LOCATION: 8

<400> SEQUENCE: 13
aaacagcuat gaagagcgcg ctgaccttta gc 32

<210> SEQ ID NO 14
<211> LENGTH: 29
<212> TYPE: DNA
<213> ORGANISM: Artificial Sequence
<220> FEATURE:
<223> OTHER INFORMATION: Primer KABY722, yberC0001_9420.rev
<220> FEATURE:
<221> NAME/KEY: misc_RNA
<222> LOCATION: 9

<400> SEQUENCE: 14
agggttaaut tacgcctcac gcacacgcg 29

<210> SEQ ID NO 15
<211> LENGTH: 31
<212> TYPE: DNA
<213> ORGANISM: Artificial Sequence
<220> FEATURE:
<223> OTHER INFORMATION: primer KABY733, fred.for
<220> FEATURE:
<221> NAME/KEY: misc_RNA
<222> LOCATION: 8

<400> SEQUENCE: 15
aaacagcuat gaagagcgcg ctgaccttca g 31

<210> SEQ ID NO 16
<211> LENGTH: 29
<212> TYPE: DNA
<213> ORGANISM: Artificial Sequence
<220> FEATURE:
<223> OTHER INFORMATION: Primer KABY734, fred.rev
<220> FEATURE:
<221> NAME/KEY: misc_RNA
<222> LOCATION: 9

<400> SEQUENCE: 16
agggttaaut tacgcttcac gcacacgcg 29

<210> SEQ ID NO 17
<211> LENGTH: 29
<212> TYPE: DNA
<213> ORGANISM: Artificial Sequence
<220> FEATURE:
<223> OTHER INFORMATION: Primer KABY729, bad.for
<220> FEATURE:
<221> NAME/KEY: misc_RNA
<222> LOCATION: 8

<400> SEQUENCE: 17
aaacagcuat gagcagccgt cgtctgagc 29

<210> SEQ ID NO 18
<211> LENGTH: 36
<212> TYPE: DNA
<213> ORGANISM: Artificial Sequence
<220> FEATURE:
<223> OTHER INFORMATION: Primer KABY730, bad.rev
<220> FEATURE:
<221> NAME/KEY: misc_RNA
<222> LOCATION: 9

<400> SEQUENCE: 18
agggttaaut tacacgtttt taacacgggt catcag 36

<210> SEQ ID NO 19
<211> LENGTH: 28
<212> TYPE: DNA
<213> ORGANISM: Artificial Sequence
<220> FEATURE:
<223> OTHER INFORMATION: Primer KABY741, nec.for
<220> FEATURE:
<221> NAME/KEY: misc_RNA
<222> LOCATION: 8

<400> SEQUENCE: 19
aaacagcuat gcagagcttc accccgcc 28

<210> SEQ ID NO 20
<211> LENGTH: 34
<212> TYPE: DNA
<213> ORGANISM: Artificial Sequence
<220> FEATURE:
<223> OTHER INFORMATION: Primer KABY742, nec.rev
<220> FEATURE:
<221> NAME/KEY: misc_RNA
<222> LOCATION: 9

<400> SEQUENCE: 20
agggttaaut tacgcctgct ctttaacacg cagc 34

<210> SEQ ID NO 21
<211> LENGTH: 31
<212> TYPE: DNA
<213> ORGANISM: Artificial Sequence
<220> FEATURE:
<223> OTHER INFORMATION: Primer KABY737, marc.for
<220> FEATURE:
<221> NAME/KEY: misc_RNA
<222> LOCATION: 8

<400> SEQUENCE: 21
aaacagcuat gcagcgtctg agccgtctga g 31

<210> SEQ ID NO 22
<211> LENGTH: 32
<212> TYPE: DNA
<213> ORGANISM: Artificial Sequence
<220> FEATURE:
<223> OTHER INFORMATION: Primer KABY738, marc.rev
<220> FEATURE:
<221> NAME/KEY: misc_RNA
<222> LOCATION: 9

<400> SEQUENCE: 22
agggttaaut taaacttcac gcactttcgc gc 32

<210> SEQ ID NO 23
<211> LENGTH: 24
<212> TYPE: DNA
<213> ORGANISM: Artificial Sequence
<220> FEATURE:
<223> OTHER INFORMATION: Primer O48, galK.for

<400> SEQUENCE: 23
cccagcgaga cctgaccgca gaac 24

<210> SEQ ID NO 24
<211> LENGTH: 24

-continued

<212> TYPE: DNA
<213> ORGANISM: Artificial Sequence
<220> FEATURE:
<223> OTHER INFORMATION: Primer O49, glaK.rev

<400> SEQUENCE: 24
ccccagtcca tcagcgtgac tacc 24

<210> SEQ ID NO 25
<211> LENGTH: 31
<212> TYPE: DNA
<213> ORGANISM: Artificial Sequence
<220> FEATURE:
<223> OTHER INFORMATION: Primer MP1217, yabM.for
<220> FEATURE:
<221> NAME/KEY: misc_RNA
<222> LOCATION: 8

<400> SEQUENCE: 25
aaacagcuat gaaggcgctg tggagccgtc g 31

<210> SEQ ID NO 26
<211> LENGTH: 31
<212> TYPE: DNA
<213> ORGANISM: Artificial Sequence
<220> FEATURE:
<223> OTHER INFORMATION: Primer MP1218, yabM.rev
<220> FEATURE:
<221> NAME/KEY: misc_RNA
<222> LOCATION: 9

<400> SEQUENCE: 26
agggttaauc gccagcggaa cgctcttcac g 31

<210> SEQ ID NO 27
<211> LENGTH: 203
<212> TYPE: DNA
<213> ORGANISM: Artificial Sequence
<220> FEATURE:
<223> OTHER INFORMATION: Promoter sequence PmglB_70UTR

<400> SEQUENCE: 27
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaaccaa ggaggaaaca gct 203

<210> SEQ ID NO 28
<211> LENGTH: 203
<212> TYPE: DNA
<213> ORGANISM: Artificial Sequence
<220> FEATURE:
<223> OTHER INFORMATION: Promoter sequence PmglB_70UTR_SD4

<400> SEQUENCE: 28
tgcgtcgcca ttctgtcgca acacgccaga atgcggcggc gatcactaac tcaacaaatc 60
aggcgatgta accgctttca atctgtgagt gatttcacag tatcttaaca atgtgatagc 120
tatgattgca ccgtgcctac aagcatcgtg gaggtccgtg actttcacgc atacaacaaa 180
cattaaccaa ctaggaaaca gct 203

-continued

```
<210> SEQ ID NO 29
<211> LENGTH: 291
<212> TYPE: DNA
<213> ORGANISM: Artificial Sequence
<220> FEATURE:
<223> OTHER INFORMATION: Promoter sequence PgatY_70UTR

<400> SEQUENCE: 29

cggcaaccta tgcctgatgc gacgctgaag cgtcttatca tgcctacata gcactgccac     60

gtatgtttac accgcatccg gcataaaaac acgcgcactt tgctacggct tccctatcgg    120

gaggccgttt ttttgccttt cactcctcga ataattttca tattgtcgtt tttgtgatcg    180

ttatctcgat atttaaaaac aaataatttc attatatttt gtgcctacaa gcatcgtgga    240

ggtccgtgac tttcacgcat acaacaaaca ttaaccaagg aggaaacagc t             291
```

HMO PRODUCTION

CROSS-REFERENCE TO RELATED APPLICATION

This application is a national stage entry pursuant to 35 U.S.C. § 371 of International Application No. PCT/EP2021/051468, filed on Jan. 22, 2021, which claims priority to Denmark Patent Application No. PA 2020 00087 filed Jan. 23, 2020, the contents of all of which are fully incorporated herein by reference.

TECHNICAL FIELD

The present invention relates to the field of recombinant production of biological molecules in host cells. More particularly it relates to a method for recombinant production of human milk oligosaccharides (HMO) using genetically modified cell expressing a protein of the major facilitator superfamily (MFS).

BACKGROUND OF THE INVENTION

Human milk oligosaccharides (HMOs) constitute the third largest solid component in human milk and are highly resistant to enzymatic hydrolysis. As a consequence, a substantial fraction of HMOs remains largely undigested and unabsorbed, which enables their passage through to the colon. In the colon, HMOs may serve as substrates to shape the gut ecosystem by selectively stimulating the growth of specific saccharolytic bacteria. This selectivity is viewed as beneficial for both infants and adults since strains of *Bifidobacterium* species are believed to have a positive effect on gut health (Chichlowski M. et al, (2012) J. Pediatr. Gastroenterol. Nutr. 5:251-258; Elison E. et al, (2016) Brit J. Nutr, 116:1356-1368).

Besides their prebiotic properties, HMOs have been linked to additional positive effects, which expands their field of application (Kunz C. et al, (2014) Food Oligosaccharides: Production, Analysis and Bioactivity, 1st Edition, p 5-20, Eds. Moreno J. and Luz Sanz M., John Wiley & Sons, Ltd).

The obvious health benefits of HMOs have enabled their approval for use in foods, such as infant formulas and foods, and for consumer health products. Biotechnological production of HMOs is a valuable cost-efficient and large-scale way of HMO manufacturing. It relies on genetically engineered bacteria constructed so as to express the glycosyltransferases needed for synthesis of the desired oligosaccharides and takes advantage of the bacteria's innate pool of nucleotide sugars as HMO precursors. Recent developments in biotechnological production of HMOs have made it possible to overcome certain inherent limitations of bacterial expression systems. For example, HMO-producing bacterial cells may be genetically modified to increase the limited intracellular pool of nucleotide sugars in the bacteria (WO2012112777), to improve activity of enzymes involved in the HMO production (WO2016040531), or to facilitate the secretion of synthesized HMOs into the extracellular media (WO2010142305, WO2017042382). Further, expression of genes of interest in recombinant cells may be regulated by using particular promoters or other gene expression regulators, like e.g what has recently been described in WO2019123324.

The approach described in WO2010142305 and WO2017042382 has an advantage in that it allows to reduce the metabolic burden inflicted on the producing cell by high levels of recombinant gene expression, e.g. using methods of WO2012112777, WO2016040531 or WO2019123324. This approach attracts growing attention in recombinant HMO-producing cells, e.g. there have been recently described fermentation procedures as well as several new sugar transporter genes encoding proteins that can facilitate the efflux of a recombinantly produced 2'-fucosyllactose (2'-FL), the most abundant HMO of human milk (WO2018077892, US201900323053, US201900323052). However, at present, there is no algorithm that is able to pinpoint the right transporter protein for the efflux of different recombinantly produced HMO structures among numerous bacterial proteins with predicted transporter function in multiple protein databases, e.g. UniProt, since the structures/factors defining substrate specificity of sugar transporters are still not well-studied and remain highly unpredictable.

SUMMARY OF THE INVENTION

Efficient sugar efflux transporter proteins for different recombinantly produced HMOs, and the development of recombinant cells expressing said proteins are advantageous for high-scale industrial HMO manufacturing.

This invention provides recombinant cells capable of producing a human milk oligosaccharide (HMO), wherein the cells are expressing a heterologous gene encoding a putative MFS (major facilitator superfamily) transporter protein, originating from the bacterium *Pantoea vagans*. More specifically, the invention relates to a genetically modified cell optimized to produce an oligosaccharide, in particular an HMO, comprising a recombinant nucleic acid encoding a protein having at least 80% sequence identity to the amino acid sequence of SEQ ID NO: 1 (FIG. 4). The amino acid sequence identified herein as SEQ ID NO: 1 is the amino acid sequence that is 100% identical to the amino acid sequence having the GenBank accession ID WP_048785139.1 (https://www.ncbi.nlm.nih.gov/protein/WP_048785139.1). The MFS transporter protein having the amino acid sequence of SEQ ID NO: 1 is identified herein as "Vag protein" or "Vag transporter" or "Vag", interchangeably; a nucleic acid sequence encoding Vag protein is identified herein as "vag coding nucleic acid/DNA" or "vag gene" or "vag".

The present invention shows that the use of HMO-producing recombinant cells that express the Vag protein results in very distinct improvements of the HMO manufacturing process both in terms of fermentation and purification of the HMOs. The disclosed herein recombinant cells and methods for HMO production provide both higher yields of total produced HMOs, lower by-product formation or by-product-to-product ratio, lower biomass formation per fermentation and facilitated recovery of the HMOs during downstream processing of the fermentation broth.

Surprisingly, the expression of a DNA sequence encoding Vag in different HMO-producing cells is found to be associated with the accumulation of particular HMOs in the extracellular media and the accumulation of other HMOs in the interior of producing cells, as well as an increase in total HMO production. Surprisingly, an increase in the efflux of the produced HMOs is found to be characteristic for HMOs that consist of either tri or tetra units of monosaccharides, i.e. HMOs that are trisaccharides and tetrasaccharides, e.g., 2'-fucosyllactose (2'-FL), 3-fucosyllactose (3-FL), 3'-sialyllactose (3'-SL), 6'-sialyllactose (6'-SL), lacto-N-triose 2, (LNT-2), lacto-N-neotetraose (LNnT) and lacto-N-tetraose (LNT), but not for larger oligosaccharide structures, like pentasaccharides and hexasaccharides, which accumulate inside of the producing cells. Surprisingly, it is also found that the total production of the HMOs lacto-N-neotetraose (LNnT) and lacto-N-tetraose (LNT) by the corresponding HMO-producing cells expressing Vag is also increased, while the by-product formation, e.g. para-lacto-N-neohexaose (pLNnH) and para-lacto-N-hexaose II (pLNH-II) in these cells, correspondingly, is often decreased and said by-product oligosaccharides typically accumulate in the cell interior of the HMO production systems. Further, highly unexpectedly, expression of the Vag protein in HMO-producing cells leads to a reduction in biomass formation during high-cell density fermentations and to healthier cell cultures, as it is e.g. reflected by a decrease in the number of dead cells at the end of fermentation, which makes the manufacturing process more efficient as more product is produced per biomass unit.

Accordingly, a first aspect of the invention relates to a genetically modified cell being capable of producing one or more HMOs, wherein said cell comprises a recombinant nucleic acid encoding a protein of SEQ ID NO: 1, or a functional homologue thereof with an amino acid sequence being at least 80% identical, preferably at least 85% identical, more preferably at least 90% identical to SEQ ID NO: 1.

A second aspect of the invention relates to a nucleic acid construct comprising a nucleic acid sequence(s) encoding an MFS transporter protein, wherein the nucleic acid sequence encoding the protein has at least 70% sequence identity to SEQ ID NO: 2, such as at least 80%, such as at least 85%, such as at least 95%, such as at least 99%, as well as to a genetically modified cell comprising the nucleic acid construct, which is *Escherichia coli.*

In one aspect, the nucleic acid construct comprises a nucleic acid sequence(s) encoding an MFS transporter protein, wherein the nucleic acid sequence is at least 70% identical to SEQ ID NO: 2.

A third aspect of the invention relates to a method for the production of one or more oligosaccharides, the method comprising the steps of:

(i) providing a genetically modified cell capable of producing an HMO, wherein said cell comprises a recombinant nucleic acid encoding a protein of SEQ ID NO: 1, or a functional homologue thereof with an amino acid sequence being at least 80% identical, preferably at least 85% identical, more preferably at least 90% identical to SEQ ID NO: 1;

(ii) culturing the cell according to (i) in a suitable cell culture medium to express said recombinant nucleic acid;

(iii) harvesting one or more HMOs produced in step (ii).

The invention also relates to the use of a genetically modified cell or a nucleic acid construct comprising a heterologous nucleic acid sequence encoding a Major facilitator superfamily (MFS) protein, said nucleic acid sequence having at least 70% sequence identity to SEQ ID NO: 2, for the production of one or more Human Milk Oligosaccharides (HMOs).

As mentioned above, during the culturing of genetically modified cells being capable of producing one or more HMOs and comprising a nucleic acid encoding the Vag transporter protein, it has surprisingly been found that the corresponding one or more HMOs are produced in high yields, while by-product and biomass formation is reduced. This facilitates the recovery of these HMOs during downstream processes, such as the overall recovery and purification procedure comprises less steps, procedure is generally simplified, overall time of purification is shortened and therefore recovery of the product is less laborious more economically efficient.

These effects of increased product yields and facilitation of the product recovery makes the present invention superior to the disclosures of the prior art.

Other aspects and advantageous features of the present invention are described in detail and illustrated by non-limiting working examples below.

BRIEF DESCRIPTION OF FIGURES

FIG. 4 presents SEQ ID NO: 1.

DETAILED DESCRIPTION

Figure 1A:
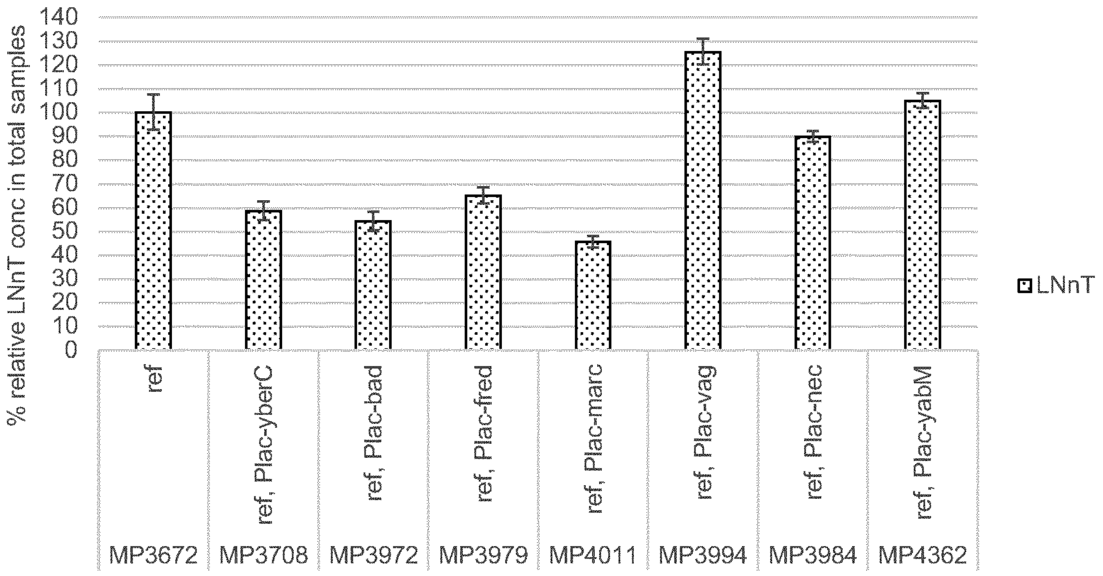
FIG. 1 shows (A) the percentage (%) relative LNnT concentrations in total samples for seven strains that express GlcNacT and Gal4T genes and a heterologous transporter gene, yberC0001_9420, bad, fred, marc, vag, nec, or yabM, correspondingly. The strain MP3672 expresses the glycosyltransferase genes and no transporter genes; (B) the percentage (%) relative LNnT concentrations in the supernatant of cells expressing vag or yabM.

In the following, embodiments of the invention will be described in further detail. Each specific variation of the features can be applied to other embodiments of the invention unless specifically stated otherwise.

Generally, all terms used herein are to be interpreted according to their ordinary meaning in the technical field, and applicable to all aspects and embodiments of the invention, unless explicitly defined or stated otherwise. All references to "a/an/the [cell, sequence, gene, transporter, step, etc]" are to be interpreted openly as referring to at least one instance of said cell, sequence, gene, transporter, step, etc., unless explicitly stated otherwise. The steps of any method disclosed herein do not have to be performed in the exact order disclosed, unless explicitly stated.

The present invention in general relates to a genetically modified cell for the efficient production of oligosaccharides and use of the said genetically modified cell in a method of producing the oligosaccharides. In particular, the present invention relates to a genetically modified cell enabled to synthesize an oligosaccharide, preferably a heterologous oligosaccharide, in particular a human milk oligosaccharide (HMO). Accordingly, a cell of the invention is modified to express a set of recombinant nucleic acids that are necessary for the synthesis of one or more HMOs by the cells (which enable the cell to synthesize one or more HMOs), such as genes encoding one or more enzymes with glycosyltransferase activity described below. The oligosaccharide producing recombinant cell of the invention is further modified to comprise a heterologous recombinant nucleic acid sequence, preferably, a DNA sequence, encoding a MFS (major facilitator superfamily) protein, originating from the bacterium *Pantoea vagans*. More specifically, the invention relates to a genetically modified cell optimized for the production of one or more particular oligosaccharides, in particular one or more particular HMOs, comprising a recombinant nucleic acid encoding a protein having at least 80% sequence similarity, preferably at least 85%, more preferably at least 90%, and even more preferably at least 95% sequence similarity to the amino acid sequence of SEQ ID NO: 1 (FIG. 4). The amino acid sequence identified herein as SEQ ID NO: 1 is an amino acid sequence that has 100% identity with the amino acid sequence having the GenBank accession ID: WP_048785139.1 (https://www.ncbi.nlm.nih.gov/protein/WP_048785139.1)

Accordingly, a first aspect of the invention relates to a genetically modified cell capable of producing one or more HMOs, wherein said cell comprises a recombinant nucleic acid encoding a protein of SEQ ID NO: 1, or a functional homologue thereof with an amino acid sequence being at least 80% identical, preferably at least 85% identical, more preferably at least 90% identical to SEQ ID NO: 1.

The MFS transporter protein having the amino acid sequence of SEQ ID NO: 1 is identified herein as "Vag protein" or "Vag transporter" or "Vag", interchangeably; a nucleic acid sequence encoding vag protein is identified here in as "vag coding nucleic acid/DNA" or "vag gene" or "vag".

By the term "Major Facilitator Superfamily (MFS)" is meant a large and exceptionally diverse family of the secondary active transporter class, which is responsible for transporting a range of different substrates, including sugars, drugs, hydrophobic molecules, peptides, organic ions, etc. The specificity of sugar transporter proteins is highly unpredictable and the identification of novel transporter protein with specificity towards, for example, oligosaccharides requires unburden laboratory experimentation (for more details see review by Reddy V. S. et al, (2012), FEBS J. 279 (11): 2022-2035). The term "MFS transporter" means in the present context a protein that facilitates transport of an oligosaccharide, preferably, an HMO, through the cell membrane, preferably transport of an HMO/oligosaccharide synthesized by the host cell from the cytosol to the cell exterior, preferably an HMO/oligosaccharide comprising three or four sugar units, in particular, 2'-FL, 3-FL, 6'-SL, DFL, LNT, LNT-2, and LNnT. Additionally, or alternatively, the MFS transporter, may also facilitate efflux of molecules which are not considered HMO or oligosaccharides according to the present invention, such as lactose, glucose, cell metabolites or toxins.

The term "sequence identity of [a certain] %" in the context of two or more nucleic acid or amino acid sequences means that the two or more sequences have nucleotides or amino acid residues in common in the given percent when compared and aligned for maximum correspondence over a comparison window or designated sequences of nucleic acids or amino acids (i.e. the sequences have at least 90 percent (%) identity). Percent identity of nucleic acid or amino acid sequences can be measured using a BLAST 2.0 sequence comparison algorithm with default parameters, or by manual alignment and visual inspection (see e.g. http://www.ncbi.nlm.nih.gov/BLAST/). This definition also applies to the complement of a test sequence and sequences that have deletions and/or additions, as well as those that have substitutions. An example of an algorithm that is suitable for determining percent identity, sequence similarity and for alignment is the BLAST 2.2.20 algorithm, which is described in Altschul et al. *Nucl. Acids Res.* 25, 3389 (1997). BLAST 2.2.20 is used to determine percent sequence identity for the nucleic acids and proteins of the invention. Software for performing BLAST analyses is publicly available through the National Center for Biotechnology Information (http://www.ncbi.nlm.nih.gov/). Examples of sequence alignment algorithms are CLUSTAL Omega (http://www.ebi.ac.uk/Tools/msa/clustalo/), EMBOSS Needle (http://www.ebi.ac.uk/Tools/psa/emboss_needle/), MAFFT (http://mafft.cbrc.jp/alignment/server/) or MUSCLE (http://www.ebi.ac.uk/Tools/msa/muscle/).

In the context of the invention, the term "oligosaccharide" means a saccharide polymer containing a number of monosaccharide units. In some embodiments, preferred oligosaccharides are saccharide polymers consisting of three or four monosaccharide units, i.e. trisaccharides or tetrasaccharides.

Preferable oligosaccharides of the invention are human milk oligosaccharides (HMOs).

The term "human milk oligosaccharide" or "HMO" in the present context means a complex carbohydrate found in human breast milk (for reference, see Urashima et al.: *Milk Oligosaccharides*. Nova Science Publisher (2011); or Chen, *Adv. Carbohydr. Chem. Biochem.* 72, 113 (2015)). The HMOs have a core structure comprising a lactose unit at the reducing end that can be elongated by one or more β-N-acetyl-lactosaminyl and/or one or more β-lacto-N-biosyl units, and this core structure can be substituted by an α-L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-triose 2 (LNT-2) lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), 3'-O-sialyllacto-N-tetraose a (LST a), fucosyl-LST a (FLST a), 6'-O-sialyllacto-N-tetraose b (LST b), fucosyl-LST b (FLST b), 6'-O-sialyllacto-N-neotetraose (LST c), fucosyl-LST c (FLST c), 3'-O-sialyllacto-N-neotetraose (LST d), fucosyl-LST d (FLST d), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT). In the context of the present invention lactose is not regarded as an HMO species.

In some embodiments of the invention, tri-HMOs and tetra-HMOs may be a preferred, e.g. trisaccharides 2'-FL, 3-FL, 6'-SL, LNT-2 and tetrasaccharides DFL, LNT, LNnT.

To be able to synthesize one or more HMOs, the recombinant cell of the invention comprises at least one recombinant nucleic acid which encodes a functional enzyme with glycosyltransferase activity. The galactosyltransferase gene may be integrated into the genome (by chromosomal integration) of the host cell, or alternatively, it may be comprised in a plasmid DNA and expressed as plasmid-borne. If two or more glycosyltransferases are needed for the production of an HMO, e.g. LNT or LNnT, two or more recombinant nucleic acids encoding different enzymes with glycosyltransferase activity may be integrated in the genome and/or expressed from a plasmid, e.g. a β-1,3-N-acetylglucosaminyltransferase (a first recombinant nucleic acid encoding a first glycosyltransferase) in combination with a β-1,4-galactosyltransferase (a second recombinant nucleic acid encoding a second glycosyltransferase) for the production of LNnT, where the first and second recombinant nucleic acid can independently from each other be integrated chromosomally or cloned on a plasmid. In one preferred embodiment, both the first and second recombinant nucleic acids are integrated into the chromosome of the production cell; in another embodiment at least one of the first and second glycosyltransferase is plasmid-borne. A protein/enzyme with glycosyltransferase activity (glycosyltransferase) may be selected in different embodiments from enzymes having the activity of α-1,2-fucosyltransferase, α-1,3-fucosyltransferase, α-1,3/4-fucosyltransferase, α-1,4-fucosyltransferase α-2,3-sialyltransferase, α-2,6-sialyltransferase, β-1,3-N-acetylglucosaminyltransferase, β-1,6-N-acetylglucosaminyltransferase, β-1,3-galactosyltransferase and β-1,4-galactosyltranserase. For example, the production of LNnT requires that the modified cell expresses an active β-1,3-N-acetylglucosaminyltransferase enzyme and an active β-1,4-galactosyltransferase enzyme. Some non-limiting embodiments of proteins having glycosyltransferase activity, which can be encoded by the recombinant genes comprised by the production cell, can be selected from non-limiting examples of Table 1.

TABLE 1

| Gene | Protein Sequence ID (GenBank) | Description | HMO example |
|---|---|---|---|
| IgtA_Nm | WP_002248149.1 | ββ-1,3-N-acetylglucosaminyl-transferase | LNT, LNnT, LNFP-I, LNFP-II, LNFP-III, LNFP-V, LNFP-VI, LNDFH-I, LNDFH-II, pLNH, F-pLNH I, pLNnH |
| IgtA_Nm_MC58 | AAF42258.1 | β-1,3-N-acetylglucosaminyl-transferase | LNT, LNnT, LNFP-I, LNFP-II, LNFP-III, LNFP-V, LNFP-VI, LNDFH-I, LNDFH-II, pLNH, F-pLNH I, pLNnH |
| IgtA_Hd | AAN05638.1 | β-1,3-N-acetylglucosaminyl-transferase | LNT, LNnT, LNFP-I, LNFP-II, LNFP-III, LNFP-V, LNFP-VI, LNDFH-I, LNDFH-II, pLNH, F-pLNH I, pLNnH |
| IgtA_Ng_PID2 | AAK70338.1 | β-1,3-N-acetylglucosaminyl-transferase | LNT, LNnT, LNFP-I, LNFP-II, LNFP-III, LNFP-V, LNFP-VI, LNDFH-I, LNDFH-II, pLNH, F-pLNH I, pLNnH |
| IgtA_Ng_NCCP11945 | ACF31229.1 | β-1,3-N-acetylglucosaminyl-transferase | LNT, LNnT, LNFP-I, LNFP-II, LNFP-III, LNFP-V, LNFP-VI, LNDFH-I, LNDFH-II, pLNH, F-pLNH I, pLNnH |
| IgtA_Past | AAK02595.1 | β-1,3-N-acetylglucosaminyl-transferase | LNT, LNnT, LNFP-I, LNFP-II, LNFP-III, LNFP-V, LNFP-VI, LNDFH-I, LNDFH-II, pLNH, F-pLNH I, pLNnH |
| IgtA_Nc | EEZ72046.1 | β-1,3-N-acetylglucosaminyl-transferase | LNT, LNnT, LNFP-I, LNFP-II, LNFP-III, LNFP-V, LNFP-VI, LNDFH-I, LNDFH-II, pLNH, F-pLNH I, pLNnH |
| IgtA_Nm_87255 | ELK60643.1 | β-1,3-N-acetylglucosaminyl-transferase | LNT, LNnT, LNFP-I, LNFP-II, LNFP-III, LNFP-V, LNFP-VI, LNDFH-I, LNDFH-II, pLNH, F-pLNH I, pLNnH |
| galT_Hp/HP0826 | NP_207619.1 | ββ-1,4-galactosyltransferase | LNnT, LNFP-III, LNFP-VI, pLNH I, F-pLNH I, pLNnH |
| galT_Nm/IgtB | AAF42257.1 | β-1,4-galactosyltransferase | LNnT, LNFP-III, LNFP-VI, pLNH I, F-pLNH I, pLNnH |

TABLE 1-continued

| Gene | Protein Sequence ID (GenBank) | Description | HMO example |
|---|---|---|---|
| wbgO | WP_000582563.1 | β-1,3-galactosyltransferase | LNT, LNFP-I, LNFP-II, LNFP-V, LNDFH-I, LNDFH-II, pLNH, F-pLNH I |
| cpsIBJ | AB050723.1 | ββ-1,3-galactosyltransferase | LNT, LNFP-I, LNFP-II, LNFP-V, LNDFH-I, LNDFH-II, pLNH, F-pLNH I |
| jhp0563 | AEZ55696.1 | β-1,3-galactosyltransferase | LNT, LNFP-I, LNFP-II, LNFP-V, LNDFH-I, LNDFH-II, pLNH, F-pLNH I |
| galTK | homologous to BD182026 | β-1,3-galactosyltransferase | LNT, LNFP-I, LNFP-II, LNFP-V, LNDFH-I, LNDFH-II, pLNH, F-pLNH I |
| futC | WP_080473865.1 | α-1,2-fucosyl-transferase | 2'-FL, DFL, LNFP-I, LNDFH-I |
| FucT2_HpUA802 | AAC99764.1 | α-1,2-fucosyl-transferase | 2'-FL, DFL, LNFP-I, LNDFH-I |
| FucT2_EcO126t | ABE98421.1 | α-1,2-fucosyl-transferase | 2'-FL, DFL, LNFP-I, LNDFH-I |
| FucT2_Hm12198 | CBG40460.1 | α-1,2-fucosyl-transferase | 2'-FL, DFL, LNFP-I, LNDFH-I |
| FucT2_Pm9515 | ABM71599.1 | α-1,2-fucosyl-transferase | 2'-FL, DFL, LNFP-I, LNDFH-I |
| FucT2_HpF57 | BAJ59215.1 | α-1,2-fucosyl-transferase | 2'-FL, DFL, LNFP-I, LNDFH-I |
| FucT6_3_Bf | CAH09151.1 | α-1,3-fucosyl-transferase | 2'-FL, 3-FL, DFL, LNFP-I, LNFP-III, LNFP-V, LNFP-VI, LNDFH-II, F-pLNH I |
| FucT7_3_Bf | CAH09495.1 | α-1,3-fucosyl-transferase | 2'-FL, 3-FL, DFL, LNFP-I, LNFP-III, LNFP-V, LNFP-VI, LNDFH-II, F-pLNH I |
| FucT_3_Am | ACD04596.1 | α-1,3-fucosyl-transferase | 2'-FL, 3-FL, DFL, LNFP-I, LNFP-III, LNFP-V, LNFP-VI, LNDFH-II, F-pLNH I |
| MAMA_R764 | AGC02224.1 | α-1,3-fucosyl-transferase | 2'-FL, 3-FL, DFL, LNFP-I, LNFP-III, LNFP-V, LNFP-VI, LNDFH-II, F-pLNH I |
| Mg791 | AEQ33441.1 | α-1,3-fucosyl-transferase | 2'-FL, 3-FL, DFL, LNFP-I, LNFP-III, LNFP-V, LNFP-VI, LNDFH-II, F-pLNH I |
| Moumou_00703 | YP_007354660 | α-1,3-fucosyl-transferase | 2'-FL, 3-FL, DFL, LNFP-I, LNFP-III, LNFP-V, LNFP-VI, LNDFH-II, F-pLNH I |
| futA | NP 207177.1 | α-1,3-fucosyl-transferase | 2'-FL, 3-FL, DFL, LNFP-I, LNFP-III, LNFP-V, LNFP-VI, LNDFH-II, F-pLNH I |
| fucT | AAB81031.1 | α-1,3-fucosyl-transferase | 2'-FL, 3-FL, DFL, LNFP-I, LNFP-III, LNFP-V, LNFP-VI, LNDFH-II, F-pLNH I |
| fucTIII | AY450598.1 | α-1,4-fucosyl-transferase | LNDFH-I, LNDFH-II |
| fucTa | AF194963.1 | α-1,3/4-fucosyl-transferase | LNFP-II, LNDFH-I, LNDFH-II |
| Pd2, 6ST | BAA25316.1 | α-2,6-sialyltransferase | 6'-SL |
| PspST6 | BAF92026.1 | α-2,6-sialyltransferase | 6'-SL |
| PIST6_145 | BAF91416.1 | α-2,6-sialyltransferase | 6'-SL |
| PIST6_119 | BAI49484.1 | α-2,6-sialyltransferase | 6'-SL |
| NST | AAC44541.1 | α-2,3-sialyltransferase | 3'-SL |

An aspect of the present invention is the provision of a nucleic acid construct comprising a heterologous nucleic acid sequence(s) encoding a protein capable of sugar transportation which is a major facilitator superfamily (MFS) protein as shown in SEQ ID NO: 1, or a functional homologue thereof which amino acid sequence is at least 80% identical to SEQ ID NO: 1, wherein the nucleic acid sequence encoding the MFS protein has at least 70% sequence identity to SEQ ID NO: 2.

By the term "heterologous nucleic acid sequence", "recombinant gene/nucleic acid/DNA encoding" or "coding nucleic acid sequence" is meant an artificial nucleic acid sequence (i.e. produced in vitro using standard laboratory methods for making nucleic acid sequences) that comprises a set of consecutive, non-overlapping triplets (codons) which is transcribed into mRNA and translated into a polypeptide when placed under the control of the appropriate control sequences, i.e. promoter. The boundaries of the coding sequence are generally determined by a ribosome binding site located just upstream of the open reading frame at the 5'end of the mRNA, a translational start codon (AUG, GUG or UUG), and a translational stop codon (UAA, UGA or UAG). A coding sequence can include, but is not limited to, genomic DNA, cDNA, synthetic, and recombinant nucleic acid sequences. The term "nucleic acid" includes RNA, DNA and cDNA molecules. It is understood that, as a result of the degeneracy of the genetic code, a multitude of nucleotide sequences encoding a given protein may be produced. The term nucleic acid is used interchangeably with the term "polynucleotide". An "oligonucleotide" is a short chain nucleic acid molecule. "Primer" is an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single-stranded for maximum efficiency in amplification but may alternatively be double-stranded. If double-stranded, the primer is first treated to separate its strands before being used to prepare extension products. Preferably, the primer is a deoxyribonucleotide. The primer must be sufficiently long to prime the synthesis of extension products in the presence of the inducing agent. The exact lengths of the primers will depend on many factors, including temperature, source of primer and the use of the method.

The recombinant nucleic sequence of the invention may be a coding DNA sequence, e.g. a gene, or non-coding DNA sequence, e.g. a regulatory DNA, such as a promoter sequence. One aspect of the invention relates to providing a recombinant cell comprising recombinant DNA sequences encoding enzymes necessary for the production of one or more HMOs, and a DNA sequence encoding the Vag transporter. Accordingly, in one embodiment the invention relates to a nucleic acid construct comprising a coding nucleic sequence, i.e. recombinant DNA sequence of a gene of interest, e.g. a glycosyltransferase gene or the vag gene, and a non-coding DNA sequence, e.g. a promoter DNA sequence, e.g. a recombinant promoter sequence derived from the promoter of the lac operon or an glp operon, or a promoter sequence derived from another genomic promoter DNA sequence, or a synthetic promoter sequence, wherein the coding and promoter sequences are operably linked. The term "operably linked" refers to a functional relationship between two or more nucleic acid (e.g., DNA) segments. Typically, it refers to the functional relationship of a transcriptional regulatory sequence to a transcribed sequence. For example, a promoter sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting.

In one embodiment, the nucleic acid construct of the invention may be a part of the vector DNA, in another embodiment, the construct is an expression cassette/cartridge that is integrated in the genome of a host cell. Accordingly, the term "nucleic acid construct" means an artificially constructed segment of nucleic acid, in particular a DNA segment, which is intended to be 'transplanted' into a target cell, e.g. a bacterial cell, to modify the expression of a host gene or express a gene/coding DNA sequence which may be included in the construct. In the context of the invention, the nucleic acid construct contains a recombinant DNA sequence comprising two or more recombinant DNA sequences: essentially, a non-coding DNA sequence comprising a promoter DNA sequence and a coding DNA sequence encoding a protein of interest, e.g. the Vag protein, a glycosyltransferase, or another protein useful for the production of an HMO in a host cell. Preferably, the construct comprises further non-coding DNA sequences that either regulate transcription or translation of the coding DNA of the construct, e.g. a DNA sequence facilitating ribosome binding to the transcript, a leading DNA sequence that stabilize the transcript, or a transcription terminator sequence.

Integration of the recombinant gene of interest comprised in the construct (i.e., expression cassette) into the bacterial genome can be achieved by conventional methods, e.g. by using linear cartridges that contain flanking sequences homologous to a specific site on the chromosome, as described for the attTn7-site (Waddell C. S. and Craig N. L., *Genes Dev.* (1988) February; 2 (2): 137-49.); methods for genomic integration of nucleic acid sequences in which recombination is mediated by the Red recombinase function of the phage λ or the RecE/RecT recombinase function of the Rac prophage (Murphy, *J Bacteriol.* (1998); 180 (8): 2063-7; Zhang et al., *Nature Genetics* (1998) 20:123-128 Muyrers et al., EMBO Rep. (2000) 1 (3): 239-243); methods based on Red/ET recombination (Wenzel et al., *Chem Biol.* (2005), 12 (3): 349-56.; Vetcher et al., *Appl Environ Microbiol.* (2005); 71 (4): 1829-35); or positive clones, i.e. clones that carry the expression cassette, can be selected e.g. by means of a marker gene, or loss or gain of gene function.

A single copy of the expression cassette comprising a gene of interest may be sufficient to secure production of a desired HMO and achieve the desired effects according to the invention. Accordingly, in some preferred embodiments, the invention relates to a recombinant HMO-producing cell that comprises one, two or three copies of a gene of interest integrated in the genomic DNA of the cell. In some embodiments, the single copy of a gene is preferred.

In one preferred embodiment, recombinant coding nucleic acid sequence of the nucleic acid construct of the invention is heterologous with respect to the promoter, which means that in the equivalent native coding sequence in the genome of species of origin is transcribed under the control of another promoter sequence (i.e. not the promoter sequence of the construct). Still, with respect to the host cell, the coding DNA may be either heterologous (i.e. derived from another biological species or genus), such as e.g. the DNA sequence encoding the Vag protein expressed in *Escherichia coli* host cells, or homologous (i.e. derived from the host cell), such as e.g. genes of the colonic acid operon, the GMAB genes.

The term, a "regulatory element" or "promoter" or "promoter region" or "promoter element" is a nucleic acid sequence that is recognized and bound by a DNA-dependent RNA polymerase during initiation of transcription. The promoter, together with other transcriptional and translational regulatory nucleic acid sequences (also termed "control sequences") is necessary to express a given gene or group of genes (i.e., an operon). In general, the transcriptional and translational regulatory sequences include, but are not limited to, promoter sequences, ribosomal binding sites, transcriptional start and stop sequences, translational start and stop sequences, transcription terminator and enhancer or activator sequences. The "transcription start site" means the first nucleotide to be transcribed and is designated +1. Nucleotides downstream of the start site are numbered +2, +3, +4 etc., and nucleotides in the 5' opposite (upstream) direction are numbered −1, −2, −3 etc. The promoter DNA sequence of the construct can derive from a promoter region of any gene of the genome of a selected species, preferably, a promoter region of the genomic DNA of *E. coli*. Accordingly, any promoter DNA sequence that can bind to an RNA polymerase and initiate transcription is suitable for practicing the invention. In principle, any promoter DNA sequence can be used to control transcription of the recombinant gene of interest of the construct, different or same promoter sequences may be used to drive transcription of different genes of interest integrated in the genome of the host cell or in an expression vector DNA. To have an optimal expression of the recombinant gene(s) included in the construct, the construct may comprise further regulatory sequences, e.g. a leading DNA sequence, such as a DNA sequence derived from 5'-untranslated region (5'UTR) of a glp gene of *E. coli*, a sequence for ribosomal binding. Examples of the later sequences are described in WO2019123324 (incorporated herein by reference) and illustrated in non-limiting working examples herein.

In some preferred embodiments, the regulatory element for the regulation of the expression of a recombinant gene included in the construct of the invention is glpFKX operon promoter, PglpF, in other preferred embodiments, the promoter is lac operon promoter, Plac.

In a further aspect, the regulatory element for the regulation of the expression of a recombinant gene included in the construct of the invention is the mglBAC; galactose/methyl-galactosidade transporter promoter PmglB or variants thereof such as but not limited to PmglB_70UTR of SEQ ID NO: 27, or PmglB_70UTR_SD4 of SEQ ID NO: 28.

In a further aspect, the regulatory element for the regulation of the expression of a recombinant gene included in the construct of the invention is the gatYZA-BCD; tagatose-1,6-bisP aldolase promoter PgatY or variants thereof such as but not limited to PgatY_U70UTR of SEQ ID NO: 29.

A currently preferred regulatory element present in a genetically modified cell and/or in a nucleic acid construct of the present invention, is selected from the group consisting of PgatY_70UTR, PglpF, PglpF_SD1, PglpF_SD10, PglpF_SD2, PglpF_SD3, PglpF_SD4, PglpF_SD5, PglpF_SD6, PglpF_SD7, PglpF_SD8, PglpF_SD9, Plac_16UTR, Plac, PmglB_70UTR and PmglB_70UTR_SD4.

An especially preferred regulatory elements present in a genetically modified cell and/or in a nucleic acid construct of the present invention, is selected from the group consisting of PglpF and Plac.

However, any promoter enabling transcription and/or regulation of the level of transcription of one or more recombinant nucleic acids that encode one or more proteins (or one or more regulatory nucleic acids) that are either necessary or beneficial to achieve an optimal level of biosynthetic production of one or more HMOs in the host cell, e.g. glucosyltransferases, proteins involved in the transmembrane transport of an HMO or HMO precursor, gene expression regulatory proteins, etc, and allowing to achieve the desired effects according to the invention is suitable for practicing the invention.

Preferably, the construct of the invention comprising a gene related to the biosynthetic production of an HMO, a promoter DNA sequence, and other regulatory sequences, such as a ribosomal binding site sequence (e.g. Shine-Dalgarno sequence), expressed in the host cell enables the production of the HMO at the level of at least 0,03 g/OD (optical density) of 1 liter of the fermentation media comprising a suspension of host cells, e.g., at the level of around 0.05 g/l/OD, around 0.1 g/l/OD, or more. For the purposes of the invention, the latter level of HMO production is regarded as "sufficient" or "optimal" and the host cell capable of producing this level of a desired HMO is regarded as "suitable host cell", i.e. the cell can be further modified to express the HMO transporter protein, e.g. Vag, to achieve at least one effect described herein that is advantageous for the HMO production.

The genetically modified cell and/or the nucleic acid construct of the present invention comprises a nucleic acid sequence such as a heterologous gene encoding a putative MFS (major facilitator superfamily) transporter protein.

An MFS transport protein of particular interest in the present invention is Vag protein. A nucleic acid construct of the present invention therefore contains a nucleic acid sequence having at least 70% sequence identity to the gene, vag, SEQ ID NO: 2.

The nucleic acid sequence contained in the genetically modified cell or in nucleic acid construct encodes for a protein of SEQ ID NO: 1, or a functional homologue thereof which amino acid sequence is at least 80% identical to SEQ ID NO: 1.

A functional homologue of the protein of SEQ ID NO: 1, may be obtained by mutagenesis. The functional homologue should have a remaining functionality of at least 50%, such as 60%, 70%, 80%, 90% or 100% compared to the functionality of amino acid sequence of SEQ ID NO: 1. The functional homologue can have a higher functionality compared to the functionality of amino acid sequence of SEQ ID NO: 1. The functional homologue of SEQ ID NO: 1, should be able to enhance HMO production of the genetically modified cell according to the invention.

The genetically modified cell (host cell or recombinant cell) may be e.g. a bacterial or yeast cell. In one preferred embodiment, the genetically modified cell is bacterial. Regarding the bacterial host cells, there are, in principle, no limitations; they may be eubacteria (gram-positive or gram-negative) or archaebacteria, as long as they allow genetic manipulation for insertion of a gene of interest and can be cultivated on a manufacturing scale. Preferably, the host cell has the property to allow cultivation to high cell densities. Non-limiting examples of bacterial host cells that are suitable for recombinant industrial production of an HMO(s) according to the invention could be *Erwinia herbicola*

(*Pantoea agglomerans*), *Citrobacter freundii, Pantoea citrea, Pectobacterium carotovorum*, or *Xanthomonas campestris*. Bacteria of the genus *Bacillus* may also be used, including *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus*, and *Bacillus circulans*. Similarly, bacteria of the genera *Lactobacillus* and *Lactococcus* may be modified using the methods of this invention, including but not limited to *Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii*, and *Lactococcus lactis*. *Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bifidobacterium* (e.g., *Bifidobacterium longum, Bifidobacterium infantis*, and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*). Bacteria comprising the characteristics described herein are cultured in the presence of lactose, and an oligosaccharide, such as an HMO, produced by the cell is retrieved, either from the bacterium itself or from a culture supernatant of the bacterium. In one preferred embodiment, the genetically modified cell of the invention is an *Escherichia coli* cell.

In another preferred embodiment, the host cell is a yeast cell e.g. *Saccharomyces cerevisiae, Schizosaccharomyces pombe, Pichia pastoris, Kluveromyces lactis, Kluveromyces marxianus*, etc.

The HMOs produced by recombinant cells of the invention may be purified using a suitable procedure available in the art (e.g. such as described in WO2015188834, WO2017182965 or WO2017152918).Genetically modified cells of the invention can be provided using standard methods of the art e.g. those described in the manuals by Sambrook et al., Wilson & Walker, "Maniatise et al., and Ausubel et al.

A host cell suitable for the HMO production, e.g. *E. coli*, may comprise an endogenous β-galactosidase gene or an exogenous β-galactosidase gene, e.g. *E. coli* comprises an endogenous lacZ gene (e.g., GenBank Accession Number V00296 (GI: 41901)). For the purposes of the invention, an HMO-producing cell is genetically manipulated to either comprise any β-galactosidase gene or to comprise the inactivated version of the gene. The gene may be inactivated by a complete or partial deletion of the corresponding nucleic acid sequence from the bacterial genome, or the gene sequence is mutated in the way that it is transcribed, or, if transcribed, the transcript is not translated, or if translated to a protein (i.e. β-galactosidase), the protein does not have the corresponding enzymatic activity. In this way the HMO-producing cell accumulates an increased intracellular lactose pool, which is beneficial for the production of HMOs.

In some embodiments, the engendered cell contains a deficient sialic acid catabolic pathway. By "sialic acid catabolic pathway" is meant a sequence of reactions, usually controlled and catalyzed by enzymes, which results in the degradation of sialic acid. An exemplary sialic acid catabolic pathway described herein is the *E. coli* pathway. In this pathway, sialic acid (Neu5Ac; N-acetylneuraminic acid) is degraded by the enzymes NanA (N-acetylneuraminic acid lyase) and NanK (N-acetylmannosamine kinase) and NanE (N-acetylmannosamine-6-phosphate epimerase), all encoded from the nanATEK-yhcH operon, and repressed by NanR (http://ecocyc.org/ECOLI). A deficient sialic acid catabolic pathway is rendered in the *E. coli* host by introducing a mutation in the endogenous nanA (N-acetylneuraminate lyase) (e.g., GenBank Accession Number D00067.1 (GL216588)) and/or nanK (N-acetylmannosamine kinase) genes (e.g., GenBank Accession Number (amino acid) BAE77265.1 (GL85676015)), and/or nanE (N-acetylmannosamine-6-phosphate epimerase, GI: 947745, incorporated herein by reference). Optionally, the nanT (N-acetylneuraminate transporter) gene is also inactivated or mutated. Other intermediates of sialic acid metabolism include: (ManNAc-6-P)N-acetylmannosamine-6-phosphate; (GlcNAc-6-P)N-acetylglucosamine-6-phosphate; (GlcN-6-P) Glucosamine-6-phosphate, and (Fruc-6-P) Fructose-6-phosphate. In some preferred embodiments, nanA is mutated. In other preferred embodiments, nanA and nanK are mutated, while nanE remains functional. In another preferred embodiment, nanA and nanE are mutated, while nanK has not been mutated, inactivated or deleted. A mutation is one or more changes in the nucleic acid sequence coding the gene product of nanA, nanK, nanE, and/or nanT. For example, the mutation may be 1, 2, up to 5, up to 10, up to 25, up to 50 or up to 100 changes in the nucleic acid sequence. For example, the nanA, nanK, nanE, and/or nanT genes are mutated by a null mutation. Null mutations as described herein encompass amino acid substitutions, additions, deletions, or insertions, which either cause a loss of function of the enzyme (i.e. reduced or no activity) or loss of the enzyme (i.e. no gene product). By "deleted" is meant that the coding region is removed completely or in part such that no (functional) gene product is produced. By inactivated is meant that the coding sequence has been altered such that the resulting gene product is functionally inactive or encodes for a gene product with less than 100%, e.g. 90%, 80%, 70%, 60%, 50%, 40%, 30% or 20% of the activity of the native, naturally occurring, endogenous gene product. A "not mutated" gene or protein does not differ from a native, naturally-occurring, or endogenous coding sequence by 1, 2, up to 5, up to 10, up to 20, up to 50, up to 100, up to 200 or up to 500 or more codons, or to the corresponding encoded amino acid sequence.

Furthermore, the host cell (e.g., *E. coli*) also comprises a sialic acid synthetic capability. For example, the bacterium comprises a sialic acid synthetic capability through provision of an exogenous UDP-GlcNAc 2-epimerase (e.g., neuC of *Campylobacter jejuni* (GenBank AAK91727.1; GL15193223) or equivalent (e.g. neuC of *E. coli* S88 (GenBank YP_002392936.1; GI: 218560023), a Neu5Ac synthase (e.g., neuB of *C. jejuni* (GenBank AAK91726.1; GI: 15193222) or equivalent, (e.g. *Flavobacterium limnosediminis* sialic acid synthase, GenBank GL559220424), and/or a CMP-Neu5Ac synthetase (e.g., neuA of *C. jejuni* (GenBank AAK91728.1; GI: 15193224) or equivalent, (e.g. *Vibrio brasiliensis* CMP-sialic acid synthase, GenBank GI: 493937153).

Production of neutral N-acetylglucosamine-containing HMOs in engineered bacteria and yeasts is known in the art (see e.g. Gebus C et al (2012) Carbohydrate Research 363 83-90; U.S. Pat. No. 10,519,475).

For the production of N-acetylglucosamine-containing HMOs, such as Lacto-N-triose 2 (LNT-2), Lacto-N-tetraose (LNT), Lacto-N-neotetraose (LNnT), Lacto-N-fucopentaose I (LNFP-I), Lacto-N-fucopentaose II (LNFP-II), Lacto-N- fucopentaose III (LNFP-III), Lacto-N-fucopentaose V (LNFP-V), Lacto-N-difucohexaose I (LDFH-I), Lacto-N-difucohexaose II (LDFH-II), and Lacto-N-neodifucohexaose II (LNDFH-III), the bacterium comprises a functional lacY and a dysfunctional lacZ gene, as described above, and it is engineered to comprise an exogenous UDP-GlcNAc: Gala/β-R β-3-N-acetylglucosaminyltransferase gene, or a functional variant or fragment thereof. This exogenous UDP-GlcNAc: Gala/β-R β-3-N-acetylglucosaminyltransferase gene (GlcNACT) may be obtained from any one of a number of sources (see Table 1), e.g., the IgtA gene described from *N. meningitidis* (Genbank protein Accession AAF42258.1) or *N. gonorrhoeae* (Genbank protein Accession ACF31229.1). Optionally, an additional exogenous glycosyltransferase gene may be co-expressed in the bacterium comprising an exogenous UDP-GlcNAc: Gala/β-R β-3-N-acetylglucosaminyltransferase. For example, a β-1,4-galactosyltransferase gene (Gal4T) is co-expressed with the UDP-GlcNAc: Gala/β-R β-N-acetylglucosaminyltransferase gene. This exogenous β-1,4-galactosyltransferase gene can be obtained from any one of a number of sources, e.g., the one described from *N. meningitidis*, the IgtB gene (Genbank protein Accession AAF42257.1), or from *H. pylori*, the HP0826/galT gene (Genbank protein Accession NP_207619.1). Optionally, the additional exogenous glycosyltransferase gene co-expressed in the bacterium comprising an exogenous UDP-GlcNAc: Gala/β-R β-3-N-acetylglucosaminyltransferase gene is a β-1,3-galactosyltransferase (Gal3T) gene, e.g., that described from *E. coli* 055: H7, the wbgO gene (Genbank protein Accession WP_000582563.1), or from *H. pylori*, the jhp0563 gene (Genbank protein Accession AEZ55696.1), or from *Streptococcus agalactiae* type lb 012 the cpsIBJ gene Genbank protein Accession AB050723.1). Functional variants and fragments of any of the enzymes described above are also encompassed by the disclosed invention.

A N-acetylglucosaminyltransferase gene and/or a galactosyltransferase gene, can also be operably linked to a Pglp and be expressed from the corresponding genome-integrated cassette. In one embodiment, the gene that is genome integrated is a gene encoding for a galactosyltransferase, e.g. HP0826 gene encoding for the GalT enzyme from *H. pylori* (Genbank protein Accession NP_207619.1); in another embodiment, the gene that is genome integrated is a gene encoding a β-1,3-N-acetylglucosaminyltransferase, e.g. IgtA gene from *N. meningitidis* (Genbank protein Accession AAF42258.1). In these embodiments, the second gene, i.e. a gene encoding a β-1,3-N-acetylglucosaminyltransferase or galactosyltransferase, correspondingly, may either be expressed from a genome-integrated or plasmid borne cassette. The second gene may optionally be expressed either under the control of a glp promoter or under the control of any other promoter suitable for the expression system, e.g. Plac.

Unless otherwise specified, all technical and scientific terms used herein have the same meaning as commonly understood by one of ordinary skill in the art to which this invention belongs. Singleton et al. (1994) Dictionary of Microbiology and Molecular Biology, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. Most of the nomenclature and general laboratory procedures required in this application can be found in Sambrook et al., Molecular Cloning: A Laboratory Manual, Vol. 1-3, Cold Spring Harbor Laboratory, Cold Spring Harbor, New York (2012); Wilson K. and Walker J., Principles and Techniques of Biochemistry and Molecular Biology (2010), Cambridge University Press; or in Maniatis et al., Molecular Cloning A laboratory Manual, Cold Spring Harbor Laboratory (2012); or in Ausubel et al., Current protocols in molecular biology, John Wiley and Sohns (2010). The manuals are hereinafter referred to as "Sambrook et al.", "Wilson & Walker", "Maniatis et al.", "Ausubel et al.", correspondingly.

A second aspect of the invention related to a method for the production of one or more HMOs, the method comprising the steps of:

(i) providing a genetically modified cell capable of producing an HMO, wherein said cell comprises a recombinant nucleic acid encoding a protein of SEQ ID NO: 1, or a functional homologue thereof having amino acid sequence that is at least 80% identical, preferably at least 85% identical, more preferably at least 90% identical to SEQ ID NO: 1;
(i) culturing the cell of (i) in a suitable cell culture medium to express said recombinant nucleic acid;
(ii) harvesting the HMOs produced in step (ii).

According to the invention, the term "culturing" (or "cultivating" or "cultivation", also termed "fermentation") relates to the propagation of bacterial expression cells in a controlled bioreactor according to methods known in the industry.

To produce one or more HMOs, the HMO-producing bacteria as described herein are cultivated according to the procedures known in the art in the presence of a suitable carbon source, e.g. glucose, glycerol, lactose, etc., and the produced HMO is harvested from the cultivation media and the microbial biomass formed during the cultivation process. Thereafter, the HMOs are purified according to the procedures known in the art, e.g. such as described in WO2015188834, WO2017182965 or WO2017152918, and the purified HMOs are used as nutraceuticals, pharmaceuticals, or for any other purpose, e.g. for research. Manufacturing of HMOs is typically accomplished by performing cultivation in larger volumes. The term "manufacturing" and "manufacturing scale" in the meaning of the invention defines a fermentation with a minimum volume of 5 L culture broth. Usually, a "manufacturing scale" process is defined by being capable of processing large volumes of a preparation containing the HMO or HMOs of interest and yielding amounts of the protein of interest that meet, e.g. in the case of a therapeutic compound or composition the demands for clinical trials as well as for market supply. In addition to the large volume, a manufacturing scale method, as opposed to simple lab scale methods like shake flask cultivation, is characterized by the use of the technical system of a bioreactor (fermenter) which is equipped with devices for agitation, aeration, nutrient feeding, monitoring and control of process parameters (pH, temperature, dissolved oxygen tension, back pressure, etc.). To a large extent, the behavior of an expression system in a lab-scale method, such as shake flasks, benchtop bioreactors or the deep well format described in the examples of the disclosure, does allow to predict the behavior of that system in the complex environment of a bioreactor.

Regarding the suitable cultivation medium used in the fermentation process, there are no limitations. The culture medium may be semi-defined, i.e. containing complex media compounds (e.g. yeast extract, soy peptone, casamino acids, etc.), or it may be chemically defined, without any complex compounds.

By the term "one or more HMOs" is meant that an HMO production cell may be able to produce a single HMO structure (a first HMO) or multiple HMO structures (a second, a third, etc. HMO). In some embodiments, it may be preferred a host cell that produces a single HMO, in other preferred embodiments, a host cell producing multiple HMO structures may be preferred. Non-limiting examples for host cells producing single HMO structures are 2'-FL, 3-FL, 3'-SL, 6'-SL or LNT-2 producing cells. Non-limiting examples of host cells capable of producing multiple HMO structures can be DFL, FSL, LNT, LNnT, LNFP-I, LNFP-II, LNFP-III, LNFP-IV, LNFP-V, pLNnHor-II producing cells.

The term "harvesting" in the context in the invention relates to collecting the produced HMO(s) following the termination of fermentation. In different embodiments it may include collecting the HMO(s) included in both the biomass (i.e., the host cells) and cultivation media, i.e. before/without separation of the fermentation broth from the biomass. In other embodiments, the produced HMOs may be collected separately from the biomass and fermentation broth, i.e. after/following the separation of biomass from cultivation media (i.e., fermentation broth). The separation of cells from the medium can be carried out with any of the methods well-known to the skilled person in the art, such as any suitable type of centrifugation or filtration. The separation of cells from the medium can follow immediately after harvesting the fermentation broth or be carried out at a later stage after storing the fermentation broth at appropriate conditions. Recovery of the produced HMO(s) from the remaining biomass (or total fermentation) include extraction thereof from the biomass (i.e., the production cells). It can be done by any suitable methods of the art, e.g. by sonication, boiling, homogenization, enzymatic lysis using lysozyme, or freezing and grinding.

After recovery from fermentation, HMO(s) are available for further processing and purification.

Purification of HMOs produced by fermentation can be done using a suitable procedure described in WO2016095924, WO2015188834, WO2017152918, WO2017182965, US20190119314 (all incorporated by reference).

In some embodiments of the invention, a host cell may produce several HMOs, wherein one HMO is the "product" HMO and some/all the other HMOs are "by-product" HMOs. Typically, by-product HMOs are either the major HMO precursors or products of further modification of the major HMO. In some embodiments, it may be desired to produce the product HMO in abundant amounts and by-product HMOs in minor amounts. Cells and methods for HMO production described herein allow for controlled production of an HMO product with a defined HMO profile, e.g. in one embodiment, the produced HMO mixture wherein the product HMO is a dominating HMO compared to the other HMOs (i.e. by-product HMOs) of the mixture, i.e. the product HMO is produced in higher amounts than other by-product HMOs; in other embodiments, the cell producing the same HMO mixture may be tuned to produce one or more by-product HMOs in higher amount than product HMO. For example, during the production of LNnT, the product HMO, often a significant amount of pLNnH, the by-product HMO, is produced. In another example, during the production of LNT, a significant amount of the by-product pLNH-II is produced. With the genetically modified cells of the present invention the level of pLNnH in the LNnT product can be significantly reduced.

Advantageously, the invention provides both a decreased ratio of by-product to product and an increased overall yield of the product (and/or HMOs in total). This, less by-product formation in relation to product formation facilitates an elevated product formation and increases efficiency of both the production and product recovery process, providing superior manufacturing procedure of HMOs.

In different preferred embodiments, different host cells producing either/both 2'-FL, 3-FL, 3'-SL, 6'-SL, LNT-2, DFL, FSL, LNT, LNnT, DFL, FSL, LNT, LNnT, LNFP-I, LNFP-II, LNFP-III, LNFP-IV, LNFP-V, pLNnH, pLNH-II, as the product or by-product HMO, may be selected. In one preferred embodiment, the product is LNnT and the by-product is pLNnH. In another preferred embodiment, the product is LNT and the by-product is pLNH-II.

The invention also relates to the use of a genetically modified cell and/or a nucleic acid construct according to the invention, for the production of one or more oligosaccharides, preferably one or more human milk oligosaccharide(s). In one embodiment, the genetically modified cell and/or the nucleic acid construct according to the invention is used in the production of a specific HMO selected from the group consisting of 2'-FL, 3-FL, DLF, LNT, LNT-II, LNnT, pLNH-II and pLNnH.

In an especially preferred embodiment, the genetically modified cell and/or the nucleic acid construct according to the invention is used in the production of a specific HMO selected from the group consisting of LNT, LNT-II, LNnT, and pLNH-II and pLNnH.

The invention is further illustrated by non-limiting examples and embodiments below.

EXAMPLES

Materials and Methods

Unless otherwise noted, standard techniques, vectors, control sequence elements, and other expression system elements known in the field of molecular biology are used for nucleic acid manipulation, transformation, and expression. Such standard techniques, vectors, and elements can be found, for example, in: Ausubel et al. (eds.), *Current Protocols in Molecular Biology* (1995) (John Wiley & Sons); Sambrook, Fritsch, & Maniatis (eds.), *Molecular Cloning* (1989) (Cold Spring Harbor Laboratory Press, NY); Berger & Kimmel, *Methods in Enzymology* 152: Guide to Molecular Cloning Techniques (1987) (Academic Press); Bukhari et al. (eds.), *DNA Insertion Elements*, Plasmids and Episomes (1977) (Cold Spring Harbor Laboratory Press, NY); Miller, J. H. Experiments in molecular genetics (1972.) (Cold spring Harbor Laboratory Press, NY)

The embodiments described below are selected to illustrate the invention and are not limiting the invention in any way.

Strains

The bacterial strain used, MDO, was constructed from *Escherichia coli* K12 DH1. The *E. coli* K12 DH1 genotype is: F", A-, gyrA96, recA1, relA1, endA1, thi-1, hsdR17, supE44. Strains utilized in the present Examples are described in Table 2.

TABLE 2

| Strain IDs | Product | Relevant Genotype |
|---|---|---|
| DH1 | — | $F^-\lambda^-$ endA1 recA1 relA1 gyrA96 thi-1 glnV44 hsdR17($r_K^-m_K^-$) |
| MDO | — | E coli DH1 ΔlacZ, ΔlacA, ΔnanKETA, ΔmelA, ΔwcaJ, ΔmdoH |

TABLE 2-continued

| Strain IDs | Product | Relevant Genotype |
|---|---|---|
| MP3672 | LNnT | MDO PglpF-GlcNACT PglpF-Gal4T (version 1)* |
| MP3708 | | MDO PglpF-GlcNAcT PglpF-Gal4T Plac-yberC0001_9420 |
| MP3972 | | MDO PglpF-GlcNAcT PglpF-Gal4T Plac-bad |
| MP3979 | | MDO PglpF-GlcNAcT PglpF-Gal4T Plac-fred |
| MP4011 | | MDO PglpF-GlcNAcT PglpF-Gal4T Plac-marc |
| MP3994 | | MDO PglpF-GlcNAcT PglpF-Gal4T Plac-vag (version 1)** |
| MP3984 | | MDO PglpF-GlcNAcT PglpF-Gal4T Plac-nec |
| MP4362 | | MDO PglpF-GlcNAcT PglpF-Gal4T Plac-yabM |
| MP3020 | | MDO PglpF-GlcNACT PglpF-Gal4T(version 2)* |
| MP4064 | | MDO PglpF-GlcNAcT PglpF-Gal4T PglpF-vag |
| MP4065 | | MDO PglpF-GlcNAcT PglpF-Gal4T Plac-vag (version 2)** |
| MP4473 | LNT | MDO PglpF-GlcNAcT PglpF-Gal3T |
| MP4546 | | MDO PglpF-GlcNAcT PglpF-Gal3T PglpF-vag |

*Strains MP3672 and MP3020 bear the same heterologous GlcNAcT and Gal4T, but differ in the copy number of the corresponding GlcNAcT-encoding gene
**Strains MP3994 and MP4065 bear the same heterologous GlcNAcT and Gal4T, but differ in the copy number of the corresponding GlcNAcT-encoding gene Media The Luria Broth (LB) medium was made using LB Broth Powder, Millers (Fisher Scientific) and LB agar plates were made using LB Agar Powder, Millers (Fisher Scientific). When appropriated ampicillin ((100 µg/mL) or any appropriated antibiotic), and/or chloramphenicol (20 µg/mL) was added.

Basal Minimal medium had the following composition: NaOH (1 g/L), KOH (2.5 g/L), $KH_2PO_4$ (7 g/L), $NH_4H_2PO_4$ (7 g/L), Citric acid (0.5 g/l), Trace mineral solution (5 mL/L). The trace mineral stock solution contained: $ZnSO_4*7H_2O$ 0.82 g/L, Citric acid 20 g/L, $MnSO_4*H_2O$ 0.98 g/L, $FeSO_4*7H_2O$ 3.925 g/L, $CuSO_4*5H_2O$ 0.2 g/L. The pH of the Basal Minimal Medium was adjusted to 7.0 with 5 N NaOH and autoclaved. Before inoculation the Basal Minimal medium was supplied with 1 mM $MgSO_4$, 4 µg/mL thiamin, 0.5% of a given carbon source (glycerol (Carbosynth)), and when appropriated Isopropyl-β-D-Thiogalactoside (IPTG) (0.2 mM) was added. Thiamin, antibiotics, and IPTG were sterilized by filtration. All percentage concentrations for glycerol are expressed as v/v and for glucose as w/v.

M9 plates containing 2-deoxy-galactose had the following composition: 15 g/L agar (Fisher Scientific), 2.26 g/L 5×M9 Minimal Salt (Sigma-Aldrich), 2 mM $MgSO_4$, 4 µg/mL thiamine, 0.2% glycerol, and 0.2% 2-deoxy-D-galactose (Carbosynth).

MacConkey indicator plates had the following composition: 40 g/L MacConkey agar Base (BD Difco™) and a carbon source at a final concentration of 1%.

Cultivation

Unless otherwise noted, *E. coli* strains were propagated in Luria-Bertani (LB) medium containing 0.2% glucose at 37° C. with agitation. Agar plates were incubated at 37° C. overnight.

Chemical Competent Cells and Transformations

*E. coli* was inoculated from LB plates in 5 mL LB containing 0.2% glucose at 37° C. with shaking until OD600 ~0.4. 2 mL culture was harvested by centrifugation for 25 seconds at 13.000 g. The supernatant was removed, and the cell pellet resuspended in 600 µL cold TB solutions (10 mM PIPES, 15 mM $CaCl_2$), 250 mM KCl). The cells were incubated on ice for 20 minutes followed by pelleting for 15 seconds at 13.000 g. The supernatant was removed, and the cell pellet resuspended in 100 µL cold TB solution. Transformation of plasmids were done using 100 µL competent cells and 1-10 ng plasmid DNA. Cells and DNA were incubated on ice for 20 minutes before heat shocking at 42° C. for 45 seconds. After 2 min incubation on ice 400 µL SOC (20 g/L tryptone, 5 g/L Yeast extract, 0.5 g/L NaCl, 0.186 g/L KCl, 10 mM $MgCl_2$, 10 mM $MgSO_4$ and 20 mM glucose) was added and the cell culture was incubated at 37° C. with shaking for 1 hour before plating on selective plates.

Plasmid were transformed into TOP10 chemical competent cells at conditions recommended by the supplier (ThermoFisher Scientific).

DNA Techniques

Plasmid DNA from *E. coli* was isolated using the QIAprep Spin Miniprep kit (Qiagen). Chromosomal DNA from *E. coli* was isolated using the QIAmp DNA Mini Kit (Qiagen). PCR products were purified using the QIAquick PCR Purification Kit (Qiagen). DreamTaq PCR Master Mix (Thermofisher), Phusion U hot start PCR master mix (Thermofisher), USER Enzyme (New England Biolab) were used as recommended by the supplier. Primers were supplied by Eurofins Genomics, Germany. PCR fragments and plasmids were sequenced by Eurofins Genomics. Colony PCR was done using DreamTaq PCR Master Mix in a T100™ Thermal Cycler (Bio-Rad).

TABLE 3

Oligos used for amplification of plasmid backbones, promoter elements, and genes of interest

| Name | SEQ ID NO | Oligonucleotide Sequence 5'-3' | Description |
|---|---|---|---|
| O40 | 5 | ATTAACCCUCCAGGCATCAAATAAAACGAAAGGC | Backbone.for |
| O68 | 6 | ATGCGCAAAUTGTGAGTTAGCTCACTCATTAG | Plac.for |
| O79 | 7 | ATTTGCGCAUCACCAATCAAATTCACGCGGCC | Backbone.rev |
| O113 | 8 | AGCTGTTUCCTCCTTAGGTACCCAGCTTTTGTTCCC | Plac.rev |
| O261 | 9 | ATGCGCAAAUGCGGCACGCCTTGCAGATTACG | PglpF.for |
| O262 | 10 | AGCTGTTUCCTCCTTGGTTAATGTTTGTTGTATGCG | PglpF.rev |
| kaby745 | 11 | AAACAGCUATGAAGAGCCTGCTGACCCGTAAAC | vag.for |
| kaby746 | 12 | AGGGTTAAUTTAAACGTTTTTCACACGCGCG | vag.rev |

TABLE 3-continued

Oligos used for amplification of plasmid backbones, promoter elements, and genes of interest

| Name | SEQ ID NO | Oligonucleotide Sequence 5'-3' | Description |
|---|---|---|---|
| kaby721 | 13 | AAACAGCUATGAAGAGCGCGCTGACCTTTAGC | yberC0001_9420.for |
| kaby722 | 14 | AGGGTTAAUTTACGCCTCACGCACACGCG | yberC0001_9420.rev |
| kaby733 | 15 | AAACAGCUATGAAGAGCGCGCTGACCTTCAG | fred.for |
| kaby734 | 16 | AGGGTTAAUTTACGCTTCACGCACACGCG | fred.rev |
| kaby729 | 17 | AAACAGCUATGAGCAGCCGTCGTCTGAGC | bad.for |
| kaby730 | 18 | AGGGTTAAUTTACACGTTTTTAACACGGGTCATCAG | bad.rev |
| kaby741 | 19 | AAACAGCUATGCAGAGCTTCACCCCGCC | nec.for |
| kaby742 | 20 | AGGGTTAAUTTACGCCTGCTCTTTAACACGCAGC | nec.rev |
| kaby737 | 21 | AAACAGCUATGCAGCGTCTGAGCCGTCTGAG | marc.for |
| kaby738 | 22 | AGGGTTAAUTTAAACTTCACGCACTTTCGCGC | marc.rev |
| O48 | 23 | CCCAGCGAGACCTGACCGCAGAAC | galK.for |
| O49 | 24 | CCCCAGTCCATCAGCGTGACTACC | galK.rev |
| MP1217 | 25 | AAACAGCUATGAAGGCGCTGTGGAGCCGTCG | yabM.for |
| MP1218 | 26 | AGGGTTAAUCGCCAGCGGAACGCTCTTCACG | yabM.rev |

TABLE 4

The heterologous MFS transporter genes tested in the in microbial hosts of the present invention

| Gene | Origin of Genes | Accession Number | Protein function |
|---|---|---|---|
| yberC0001_9420 | *Yersinia bercovieri* | EEQ08298.1 | Major facilitator superfamily MFS_1 |
| fred* | *Yersinia frederiksenii* | WP_087817556.1 | MFS transporter |
| nec* | *Rosenbergiella nectarea* | WP_092672081.1 | MFS transporter |
| marc* | *Serratia marcescens* | WP_060448169.1 | MFS transporter |
| bad* | *Rouxiella badensis* | WP_017489914.1 | MFS transporter |
| vag* | *Pantoea vagans* | WP_048785139.1 | MFS transporter |
| yabM | *Erwinia pyrifoliae* | CAY73138.1 | Putative MFS sugar efflux transporter |

*the gene name is given to identify the nucleic acid encoding the protein having amino acid sequence of the corresponding GenBank Accession Number for the purposes of the present invention ..

TABLE 5

The synthetic DNA elements utilized for expression of vag

| Sequence name | SEQ ID NO | Sequence (5'-3') | Description |
|---|---|---|---|
| PglpF | 3 | GCGGCACGCCTTGCAGATTACGGTTT GCCACACTTTTCATCCTTCTCCTGGTG ACATAATCCACATCAATCGAAAATGTTA ATAAATTTGTTGCGCGAATGATCTAACA AACATGCATCATGTACAATCAGATGGA ATAAATGGCGCGATAACGCTCATTTTA TGACGAGGCACACACATTTTAAGTTCG ATATTTCTCGTTTTTGCTCGTTAACGAT AAGTTTACAGCATGCCTACAAGCATCG TGGAGGTCCGTGACTTTCACGCATACA ACAAACATTAACCAAGGAGGAAACAGC T | 300-nucleotide DNA expression element |

TABLE 5-continued

The synthetic DNA elements utilized for expression of vag

| Sequence name | SEQ ID NO | Sequence (5'-3') | Description |
|---|---|---|---|
| Plac | 4 | ATGCGCAAATTGTGAGTTAGCTCACTC ATTAGGCACCCCAGGCTTTACACTTTA TGCTTCCGGCTCGTATGTTGTGTGGAA TTGTGAGCGGATAACAATTTCACACAG GAAACAGCTATGACCATGATTACGCCA AGCGCGCAATTAACCCTCACTAAAGGG AACAAAAGCTGGGTACCTAAGGAGGAA ACAGCT | 195-nucleotide DNA expression element |
| vag | 2 | ATGAAGAGCCTGCTGACCCGTAAACGT CGTATTAACCCGGTGTTCCTGGCGTTT ATGGCGGCGAGCTTCATGATCGGTGTT GCGGGTGCGCTGCAGGCGCCGACCCT GAGCCTGTTTCTGACCCGTGAGGTGC AAGCGCGTCCGCTGTGGGTGGGCCTG TTCTTTACCGTTAACGCGATCGCGGGT ATTGTGGTTAGCATGCTGGTTGCGAAG CGTAGCGACAGCCGTGGCGATCGTCG TACCCTGATTCTGTTCTGCTGCGCGAT GGCGTTTTGCAACGCGCTGCTGTTCG CGTTTACCCGTCACTACCTGACCCTGA TTACCCTGGGTGTGCTGCTGAGCGCG CTGGCGAGCGTTAGCATGCCGCAGAT TTTCGCGCTGGCGCGTGAGTATGCGG ACCAAAGCGCGCGTGAAGCGGTGATG TTTAGCAGCGTTATGCGTGCGCAGCTG AGCCTGGCGTGGGTGATTGGCCCGCC GCTGAGCTTCGCGCTGGCGCTGAACT TCGGTTTTGTGACCCTGTTCCTGGTTG CTGCGGCGCTGTTTCTGGTGTGCATCC TGCTGATTAAGTTTACCCTGCCGAGCG TTCCGCGTGCGGAACCGCTGATGCGT AGCGGTGGCATGCCGCTGAGCGGTTG GCGTGACCGTGATGTGCGTCTGCTGTT CATTGCGAGCGTTACCATGTGGACCTG CAACACCATGTACATCATTGACATGCC GCTGTATATCAGCGTTACCCTGGGTCT GCCGGAGAAACTGGCGGGTCTGCTGA TGGGCACCGCGGCGGGTCTGGAAATT CCGGTGATGCTGCTGGCGGGTCACTA TGCGAAGCGTGTTGGTAAACGTAACCT GATGCTGATTGCGGTGGCGGCGGGCG TTCTGTTCTATGCGGGTCTGGCGATGT TTGCGAGCCAGACCGCGCTGATGGCG CTGCAACTGTTCAACGCGGTGTTTATT GGCATCATTGCGGGTATCGGCATGCT GTGGTTCCAGGATCTGATGCCGGGTC GTCCGGGTGCGGCGACCACCATGTTT ACCAACAGCATCAGCACCGGTATGATT CTGGCGGGCGTTATCCAAGGCACCCT GAGCGAGCGTTTCGGCCACATTGCGG TGTATTGGCTGGCGCTGGGTCTGGCG GTTGCGGCGTTTGCGATGAGCGCGCG TGTGAAAAACGTTTAA | MFS transporter coding DNA |

Construction of Plasmids

Plasmid backbones containing two I-SceI endonuclease sites, separated by two DNA fragments appropriated for homologous recombination into the *E. coli* genome and a T1 transcriptional terminator sequence were synthesized. For example in one plasmid backbone the gal operon (required for homologous recombination in galk), and a T1 transcriptional terminator sequence (pUC57::gal) was synthesized (GeneScript). The DNA sequences used for homologous recombination in the gal operon covered base pairs 3.628.621-3.628.720 and 3.627.572-3.627.671 in sequence *Escherichia coli* K-12 MG155 complete genome GenBank: ID: CP014225.1. Insertion by homologous recombination would result in a deletion of 949 base pairs of galK and a galK-phenotype. In similar ways backbones based on pUC57 (GeneScript) or an any other appropriated vector containing two I-SceI endonuclease sites, separated by two DNA fragments appropriated for homologous recombination into the *E. coli* genome and a T1 transcriptional terminator sequence could be synthesized. Standard techniques well-known in the field of molecular biology were used for designing of primers and amplification of specific DNA sequences of the *Escherichia coli* K-12 DH1 chromosomal DNA. Such standard techniques, vectors, and elements can be found, for example, in: Ausubel et al. (eds.), *Current Protocols in Molecular Biology* (1995) (John Wiley & Sons); Sambrook, Fritsch, & Maniatis (eds.), *Molecular Cloning* (1989) (Cold Spring Harbor Laboratory Press, NY);

Berger & Kimmel, *Methods in Enzymology* 152: Guide to Molecular Cloning Techniques (1987) (Academic Press); Bukhari et al. (eds.).

Chromosomal DNA obtained from *E. coli* DH1 was used to amplify a 300 bp DNA fragment containing the promoter PglpF using oligos O261 and O262, and a 195 bp DNA fragment containing Plac using oligos 068 and 0113 (Table 3).

A 1.179 bp DNA fragment containing a codon optimized version of the vag gene originating from *Pantoea vagans* was synthesized by GeneScript (Table 5). The vag gene was amplified by PCR using oligos KABY745 and KABY746.

All PCR fragments (plasmid backbones, promoter containing elements and the vag gene) were purified, and plasmid backbones, promoter elements (PglpF, or Plac), and a vag containing DNA fragment were assembled. The plasmids were cloned by standard USER cloning. Cloning in any appropriated plasmid could be done using any standard DNA cloning techniques. The plasmids were transformed into TOP10 cells and selected on LB plates containing 100 μg/mL ampicillin (or any appropriated antibiotic) and 0.2% glucose. The constructed plasmids were purified and the promoter sequence and the 5' end of the vag gene was verified by DNA sequencing (MWG Eurofins Genomics). In this way, a genetic cassette containing any promoter of interest linked to the vag gene was constructed.

TABLE 6

Examples of helper and donor plasmids used for strain construction

| Plasmid | Relevant genotype | Marker gene |
|---|---|---|
| pACBSR | Para-I-SceI-Á Red, p15A ori, cam* | cam |
| pUC57 | pMB1, bla | bla |
| pUC57::gal | pUC57::galTK'/T1-galKM' | bla |

DNA sequences of heterologous genes coding for transporters or glycosyltransferases of interest were codon optimized and synthesized by GenScript. The genes of interest encoding for the transporter proteins as shown in Table 4 were amplified by PCR using appropriated primers covering the start codon, ATG, and the stop codon, TAA, of the gene (Table 3). To construct donor plasmids with any heterologous gene of interest, standard USER cloning was employed to combine the purified PCR fragments of the relevant plasmid backbone, promoter element and gene of interest. Cloning in an appropriated plasmid could be done using any standard DNA cloning technique. Following cloning the DNA was transformed into TOP10 cells and selected on LB plates containing 100 μg/mL ampicillin (or 50 mg/mL kanamycin depending on the backbone applied) and 0.2% glucose. The constructed plasmids were purified, and the promoter sequence and the 5'end of the gene of interest were verified by DNA sequencing (MWG Eurofins Genomics).

Construction of Strains

The bacterial strain used, MDO, was constructed from *Escherichia coli* K-12 DH1. The *E. coli* K-12 DH1 genotype is: F", A, gyrA96, recA1, relA1, endA1, thi-1, hsdR17, supE44. In addition to the *E. coli* K-12 DH1 genotype MDO has the following modifications: lacZ: deletion of 1.5 kbp, lacA: deletion of 0.5 kbp, nanKETA: deletion of 3.3 kbp, melA: deletion of 0.9 kbp, wcaJ: deletion of 0.5 kbp, mdoH: deletion of 0.5 kbp, and insertion of Plac promoter upstream of the gmd gene.

Insertion of an expression cassette containing a promoter linked to the vag gene and to a T1 transcriptional terminator sequence was performed by Gene Gorging essentially as described by Herring et al (Herring, C.D., Glasner, J. D. and Blattner, F. R. (2003). Gene (311). 153-163), and example of helper and donor plasmids used to construct strains presented in the present application are provided in Table 6. Briefly, the donor plasmid and the helper plasmid were co-transformed into MDO and selected on LB plates containing 0.2% glucose, ampicillin (100 μg/mL) or kanamycin (50 mg/mL) and chloramphenicol (20 μg/mL). A single colony was inoculated in 1 mL LB containing chloramphenicol (20 μg/mL) and 10 μL of 20% L-arabinose and incubated at 37° C. with shaking for 7 to 8 hours. For integration in the galK loci of *E. coli* cells were then plated on M9-DOG plates and incubated at 37° C. for 48 hours. Single colonies formed on MM-DOG plates were re-streaked on LB plates containing 0.2% glucose and incubated for 24 hours at 37° C. Colonies that appeared white on MacConkey-galactose agar plates and were sensitive for both ampicillin and chloramphenicol were expected to have lost the donor and the helper plasmid and contain an insertion in the galK loci. Insertions in the galK site was identified by colony PCR using primers 048 (SEQ ID NO: 23) and 049 (SEQ ID NO: 24) and the inserted DNA was verified by sequencing (Eurofins Genomics, Germany).

Insertion of genetic cassettes at other loci in the *E. coli* chromosomal DNA was done in a similar way using different selection marker genes.

Deep Well Assay (DWA)

DWA was performed as originally described to Lv et al (Bioprocess Biosyst Eng (2016) 39:1737-1747) and optimized for the purposes of the current invention. More specifically, the strains disclosed in the examples were screened in 24 deep well plates using a 4-day protocol. During the first 24 hours, cells were grown to high densities while in the next 72 hours cells were transferred to a medium that allowed induction of gene expression and product formation. Specifically, during day 1 fresh inoculums were prepared using a basal minimal medium supplemented with magnesium sulphate, thiamine and glucose. After 24 hours of incubation of the prepared cultures at 34° C. with a 700 rpm shaking, cells were transferred to a new basal minimal medium (2 ml) supplemented with magnesium sulphate and thiamine to which an initial bolus of 20% glucose solution (1 μl) and 10% lactose solution (0.1 ml) were added, then 50% sucrose solution as carbon source was provided to the cells. After inoculation of the new medium, cells were shaken at 700 rpm at 28° C. for 72 hours. After denaturation and subsequent centrifugation, the supernatants were analyzed by HPLC.

For the analysis of total samples, the cell lysate prepared by boiling was pelleted by centrifugation for 10 minutes at 4.700 rpm. The HMO concentration in the supernatant was determined by HPLC or HPAC methods.

Sequence Alignments

Heuristic pairwise sequence alignments as implemented in BLAST 2.1.2 (Basic Local Alignment Search Tool) (Altschul et al. 1990) on the NCBI database (http://www.ncbi.nlm.nih.gov) were performed to test the homology among the transporter protein sequences mentioned in the present invention. All parameters were kept at their default values for every BLAST alignment.

Results

Example 1. The Vag Transporter is a Novel LNT-2-Core Transporter with High Selectivity for LNnT In the present invention, we tested the ability of selected heterologous MFS transporters to export LNnT out of the host cell using a reference strain, namely MP3672. The strain has one PglpF-driven copy of each heterologous glycosyltransferase that is required for product formation.

One copy of each of the selected heterologous transporter genes, i.e. vag, yberC0001_9420, marc, bad, nec, yabM and fred (Table 4), was individually integrated in the genome of the strain MP3672 under the control of the Plac promoter, which is known to provide moderate transcript levels. The ribosomal binding site of the Plac promoter (i.e., the 16 bp upstream of the translational start site) has been modified (see Table 5) to strengthen ribosomal binding to the synthesized transcripts and in this manner positively regulate Plac-driven expression at the translational level.

Following the above strain engineering approach and testing strain performance in DWA, we report here that only Vag-expressing LNnT producing cells show arelative increase both in the efflux of the produced LNnT and LNnT total production, compared to the reference strain.

As shown in FIG. 1A, Plac-driven expression of most transporter genes (marc, fred, bad, nec, yabM, yberC0001_9420) either has no significant effect or diminish LNnT production (down to 45%). On the contrary introduction of the vag gene in the genetic background of the strain MP3672 results in a marked increase in LNnT titer (FIG. 1A).

Figure 1B:
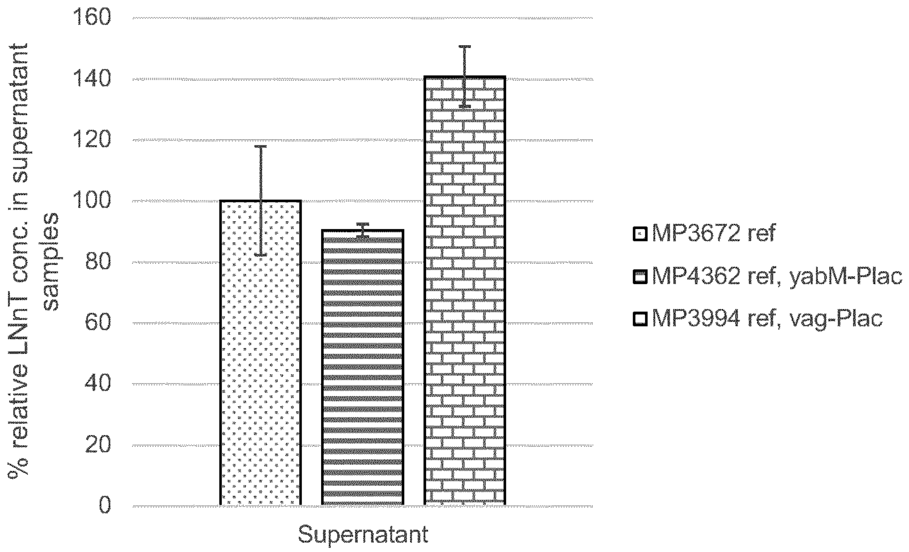

The alignment of amino acid sequences of the seven tested putative MSF transporters revealed that the Vag transporter has a very high sequence coverage (99 to 100%) to the rest six transporters tested in the present invention, with sequence identity ranging from 65% to 75%. The highest sequence identity (75%) was scored for the sequence of Vag and sequence of the MFS transporter encoded by the yabM gene (Table 7). Interestingly, the MFS transporter YabM, described in WO2017042382 as an putative effective exporter of LNT, did not show any significant impact on neither the final total LNnT titer nor LNnT efflux (FIG. 1A, 1B). Thus, contrary to its relatively high protein sequence similarity to Vag, the YabM transporter seems to be ineffective in relation to LNnT transport, which is clearly reflected by the product concentrations detected in the extracellular fraction of the corresponding host cell cultures (FIG. 1B). Specifically, as revealed by the analysis of the supernatant fractions of bacterial cultures, extracellular LNnT concentrations were much higher for the strain MP3994 (vag-expressing cells) than for the strains MP4362 (yabM-expressing cells) and MP3672 (reference cells expressing no any heterologous transporter) (FIG. 1B).

TABLE 7

Homology between different heterologous transporters of the present invention:

| Protein name | Identification | From organism | Identical to Vag WP_048785139.1 (coverage) |
|---|---|---|---|
| YberC0001_9420 | EEQ08298.1 Major facilitator superfamily MFS_1 | *Yersinia bercovieri* | 68% (99%) |
| Fred | WP_087817556.1 MFS transporter | *Yersinia frederiksenii* | 69% (99%) |
| Bad | WP_017489914.1 MFS transporter | *Rouxiella badensis* | 65% (99%) |
| Nec | WP_092672081.1 MFS transporter | *Rosenbergiella nectarea* | 66% (99%) |
| Marc | WP_060448169.1 MFS transporter | *Serratia marcescens* | 71% (99%) |
| YabM | CAY73138.1 Putative MFS sugar efflux transporter | *Erwinia pyrifoliae* | 75% (99%) |

Taken together, this data suggest that the Vag transporter is an efficient transporter for LNnT. This conclusion derives from both the results of a screening procedure of the seven transporter genes genomically expressed in the same reference strain, under the same culture conditions and control of the same promoter, Plac, and analysis of the transporter protein sequences, that revealed that transporter proteins with relatively high homology to Vag, such as YabM and Marc (75% and 71%), do not export LNnT at all, or, if export, the efficiency is very low.

Example 2. Engineering of *Escherichia coli* for LNnT Production Using the Vag Gene The *Escherichia coli* K-12 (DH1) MDO strains can be manipulated to express heterologous genes of interest. For instance, the strain MP3020 is a LNnT production strain overexpressing a β-1,3-N-acetylglucosaminyltransferase gene and a β-1,3-galactosyltransferase gene selected from non-limiting examples of Table 1.

Figure 2:
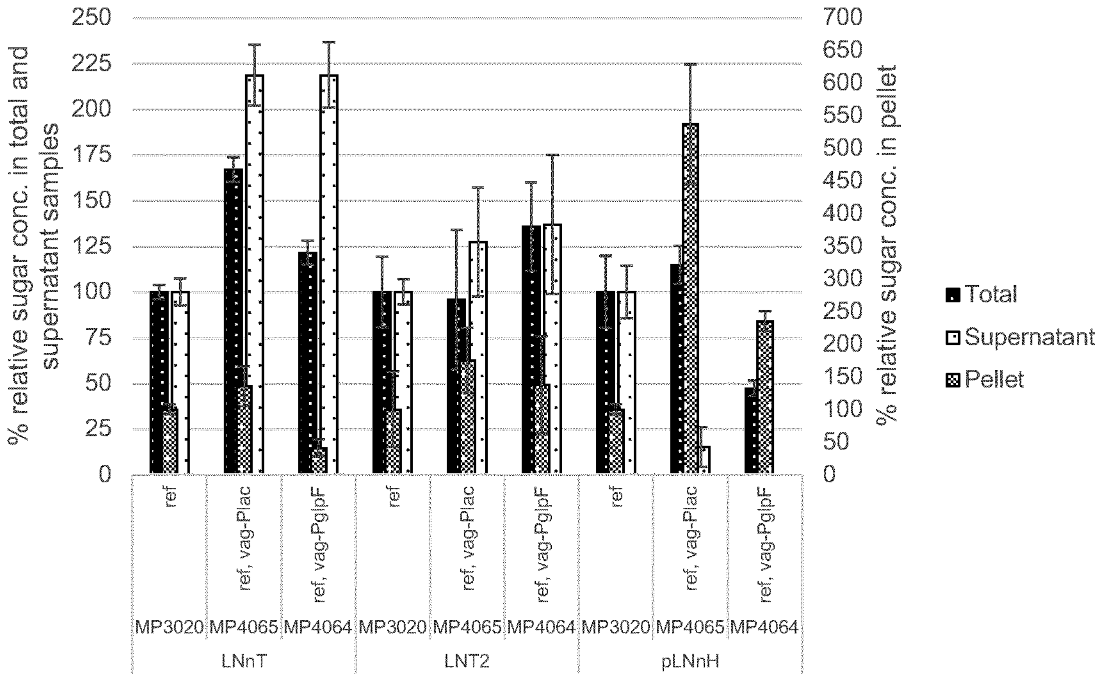
FIG. 2 shows the percentage (%) relative LNnT and by-product concentrations for the strains MP3020, MP4065 and MP4064 in total, supernatant and pellet samples. Although all three strains show optimal expression of the required glycosyltransferase genes, it is MP4065 and MP4064 that express the heterologous transporter gene vag under the control of the Plac or PglpF element, respectively.

As shown from the HPLC analysis of total samples, insertion of an expression cassette containing the promoter element PglpF or Plac linked to a vag gene into the chromosomal DNA of strain MP3020 in a single copy to generate the strains MP4064 and MP4065, respectively (Table 2), resulted in i) higher total LNnT titers, ii) similar or slightly higher total LNT-2 concentrations, and iii) similar or much lower total pLNnH formation (FIG. 2). It seems that the level of expression of the transporter gene has an effect on by-product fomation in LNnT producing strains: Plac-driven expression (relatively moderate) of the vag gene had a positive effect on total LNnT titer, which was accompanied by a minor increase in total pLNnH, but not LNT-2, titers. PglpF-driven expression (relatively high) of the vag gene led to a higher LNnT titer than the reference strain as well, but this strain (MP4064) showed slightly higher total LNT-2 titers and markedly decreased total pLNnH formation (FIG. 2).

The significant impact of introducing the vag gene in a LNnT production strain is, however, more clearly revealed by looking at the analysis of supernatant samples. The LNnT concentration in the supernatant fraction of cultures of the strains MP4064 and MP4065 is increased by more than 2-fold compared to the one measured in the medium of MP3020 cultures (FIG. 2). Although not markedly higher total LNT-2 titers are observed in transporter-expressing cells, LNT-2 in the supernatant fraction is seemingly higher in the strains MP4064 and MP4065 than in strain MP3020. As mentioned above, pLNnH formation is either slightly increased in strain MP4065, or markedly reduced in strain MP4064. Interestingly, pLNnH is found only in the cell pellet of both strains MP4064 and MP4065, which indicates that expression of the Vag transporter does not have an effect on the export of the produced pLNnH (FIG. 2).

Example 3. Engineering of *Escherichia coli* for LNT Production Using the Vag Gene The *Escherichia coli* K-12 (DH1) MDO strains can be manipulated to express heterologous genes of interest. For instance, the strain MP4473 is a LNT production strain overexpressing a β-1,3-N-acetylglucosaminyltransferase gene and a β-1,3-galactosyltransferase gene selected from Table 1.

Figure 3:
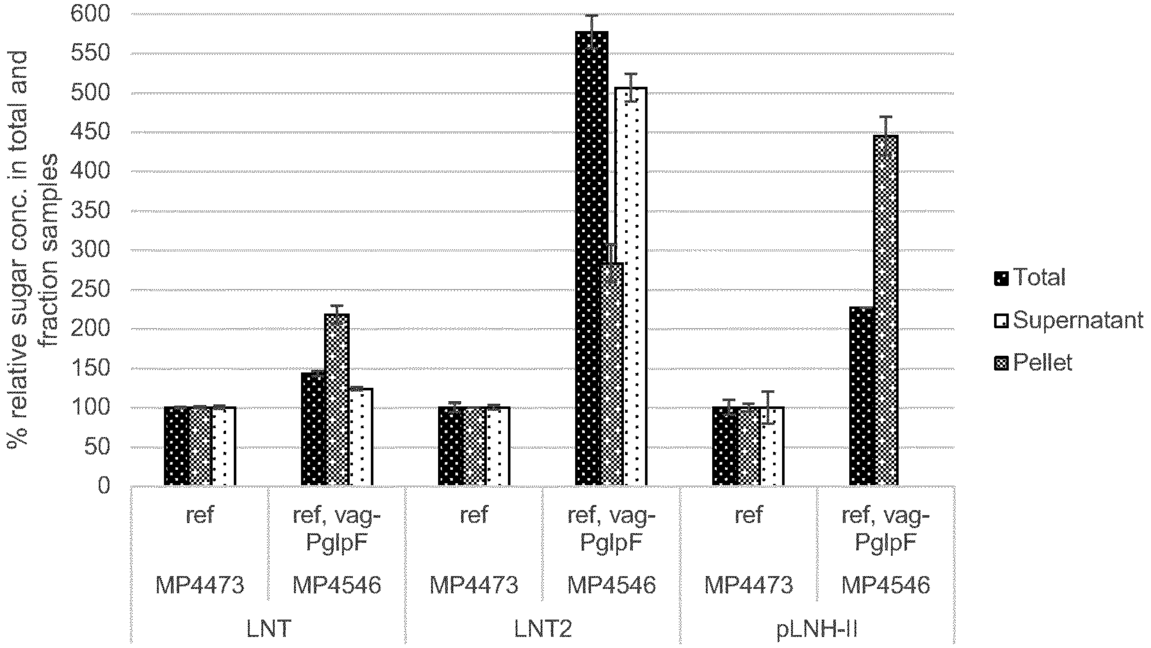
FIG. 3 shows the percentage (%) relative LNT and by-product concentrations for the strains MP4473 and MP4546 in total, supernatant and pellet samples. Although both strains show optimal expression of the required glycosyltransferase genes, it is only MP4546 that expresses the heterologous transporter gene vag under the control of the PglpF element.

As shown from the HPLC analysis of total samples, insertion of an expression cassette containing a promoter element (PglpF) linked to the vag gene into the chromosomal DNA of strain MP4473 in a single copy to generate the strain MP4546 (Table 2) resulted in i) an increase in the total LNT titer (almost 50% higher total LNT concentration than the reference strain), ii) approximately 6-fold increase in total LNT-2 concentration, and iii) approximately 2.5-fold higher total pLNH-II formation (FIG. 3).

In agreement with the observations above, the analysis of supernatant samples revealed that the LNT concentration in the supernatant fraction of cultures of the strain MP4546 is markedly increased compared to the one measured in the medium of MP4473 cultures (FIG. 3). The much higher total LNT-2 titer measured in vag-expressing cells is accompanied by the 5-fold higher LNT-2 concentration detected in the supernatant fraction of MP4546 cultures. In contrary, the produced pLNH-II seems to reside solely in the cell pellet of the strain MP4546, possibly, because of Vag has either low or no substrate specificity for pLNH-II, or it is not capable of transporting large sugars, like hexosaccharides (FIG. 3). This "lack of capability" seems to be an advantageous feature as it allows a simplified downstream processing of pLNH-II produced by vag-expressing cells because multiple different HMOs produced in a single fermentation can be separated from the HMO mix at the very first stage of the purification procedure.

The invention claimed is:

1. A genetically modified cell capable of producing one or more Human Milk Oligosaccharides (HMOs) under fermentative conditions, wherein the cell comprises a recombinant nucleic acid encoding a protein of SEQ ID NO: 1, or a functional homologue thereof which amino acid sequence is at least 90% identical to SEQ ID NO: 1, wherein the functional homologue increases the total production of the one or more HMOs while reducing by-product formation or facilitates the export of the one or more HMOs out of the genetically modified cell.

2. The genetically modified cell according to claim 1, wherein the one or more HMOs is selected from the group consisting of 2'-fucosyllactose (2'FL), 3'-fucosyllactose (3FL), difucosyllactose (DFL), 3'-sialyllactose (3'SL), 6'-sialyllactose (6'SL), Lacto-N-Triose-2 (LNT-2), Lacto-N-neotetraose (LNnT), Lacto-N-tetraose (LNT), Lacto-N-fucopentaose I (LNFP-I), Lacto-N-fucopentaose II (LNFP-II), Lacto-N-fucopentaose III (LNFP-III), Lacto-N-fucopentaose IV (LNFP-IV), and Lacto-N-fucopentaose V (LNFP-V), and/or para-lacto-N-neohexaose (pLNnH); or a mixture thereof.

3. The genetically modified cell according to claim 1, wherein the genetically modified cell is *Escherichia coli.*

4. The genetically modified cell according to claim 1, wherein the cell further comprises an expression element comprising a lac promoter or a glp promoter.

5. The genetically modified cell according to claim 4, wherein the lac promoter, if present, is Plac and the glp promoter, if present, is Pg/pF.

6. A nucleic acid construct comprising a nucleic acid sequence encoding a protein of SEQ ID NO: 1, or a functional homologue thereof, having more than 90% sequence identity to SEQ ID NO: 1, wherein the nucleic acid sequence encoding a protein of SEQ ID NO: 1, has at least 80% sequence identity to SEQ ID NO: 2.

7. The nucleic acid construct according to claim 6, wherein the construct further comprises a nucleic acid sequence comprising an expression element comprising a lac promoter or a glp promoter.

8. The nucleic acid construct according to claim 7, wherein the expression element regulates the expression of the nucleic acid sequence having at least 85% sequence identity to SEQ ID NO: 2.

9. The nucleic acid construct according to claim 7, wherein the lac promoter, if present, is Plac and the glp promoter, if present, is Pg/pF.

10. A method for the production of one or more HMOs, the method comprising the steps of:

(i) providing the genetically modified cell of claim 1;

(ii) culturing the cell according to (i) in a suitable cell culture medium to express said recombinant nucleic acid, whereby one or more HMOs are produced by the cultured genetically modified cell;

(iii) harvesting the one or more HMOs produced in step (ii).

11. The method according to claim 10, wherein the one or more HMOs is selected from the group consisting of 2'-FL, 3-FL, DLF, LNT, LNT-II, LNnT, pLNH-II and pLNnH; or a mixture thereof.

12. The method according to claim 10, wherein the one or more HMOs is selected from the group consisting of LNT, LNT-II, LNnT, and pLNH-II and pLNnH; or a mixture thereof.

13. The genetically modified cell according to claim 1, wherein the functional homologue comprises an amino acid sequence at least 95% identical to SEQ ID NO: 1.

14. The method according to claim 10, wherein the one or more HMOs is selected from the group consisting of 2'-fucosyllactose (2'FL), 3'-fucosyllactose (3FL), difucosyllactose (DFL), 3'-sialyllactose (3'SL), 6'-sialyllactose (6'SL), Lacto-N-Triose-2 (LNT-2), Lacto-N-neotetraose (LNnT), Lacto-N-tetraose (LNT), Lacto-N-fucopentaose I (LNFP-I), Lacto-N-fucopentaose II (LNFP-II), Lacto-N-fucopentaose III (LNFP-III), Lacto-N-fucopentaose IV (LNFP-IV), and Lacto-N-fucopentaose V (LNFP-V), and/or para-lacto-N-neohexaose (pLNnH); or a mixture thereof.

15. A method for the production of one or more HMOs, the method comprising the steps of:

(i) providing the genetically modified cell of claim 4;

(ii) culturing the cell according to (i) in a suitable cell culture medium to express said recombinant nucleic acid, whereby one or more HMOs are produced by the cultured genetically modified cell;

(iv) harvesting one or more HMOs produced in step (ii).

16. The method according to claim 15, wherein the one or more HMOs is selected from the group consisting of 2'-fucosyllactose (2'FL), 3'-fucosyllactose (3FL), difucosyllactose (DFL), 3'-sialyllactose (3'SL), 6'-sialyllactose (6'SL), Lacto-N-Triose-2 (LNT-2), Lacto-N-neotetraose (LNnT), Lacto-N-tetraose (LNT), Lacto-N-fucopentaose I (LNFP-I), Lacto-N-fucopentaose II (LNFP-II), Lacto-N-fucopentaose III (LNFP-III), Lacto-N-fucopentaose IV (LNFP-IV), and Lacto-N-fucopentaose V (LNFP-V), and/or para-lacto-N-neohexaose (pLNnH); or a mixture thereof.

17. The method according to claim 15, wherein the one or more HMOs is selected from the group consisting of 2'-FL, 3-FL, DLF, LNT, LNT-II, LNnT, pLNH-II and pLNnH; or a mixture thereof.

18. The method according to claim 15, wherein the one or more HMOs is selected from the group consisting of LNT, LNT-II, LNnT, and pLNH-II and pLNnH; or a mixture thereof.

* * * * *